United States Patent
Fitchmun

(10) Patent No.: US 10,540,989 B2
(45) Date of Patent: Jan. 21, 2020

(54) SOMATIC, AUDITORY AND COCHLEAR COMMUNICATION SYSTEM AND METHOD

(71) Applicant: Somatek, San Diego, CA (US)

(72) Inventor: Mark I. Fitchmun, San Diego, CA (US)

(73) Assignee: Somatek, San Diego, CA (US)

( * ) Notice: Subject to any disclaimer, the term of this patent is extended or adjusted under 35 U.S.C. 154(b) by 869 days.

(21) Appl. No.: 14/489,406

(22) Filed: Sep. 17, 2014

(65) Prior Publication Data

US 2015/0194166 A1 Jul. 9, 2015

Related U.S. Application Data

(63) Continuation of application No. 11/997,902, filed as application No. PCT/US2006/030437 on Aug. 3, 2006, now abandoned.
(Continued)

(51) Int. Cl.
*A61N 1/36* (2006.01)
*G10L 21/06* (2013.01)
(Continued)

(52) U.S. Cl.
CPC ............ *G10L 21/16* (2013.01); *A61N 1/0541* (2013.01); *G10L 15/02* (2013.01); *G10L 21/06* (2013.01);
(Continued)

(58) Field of Classification Search
CPC .. A61N 1/36032; A61N 1/0541; H04R 25/00; H04R 25/50; H04R 2225/43;
(Continued)

(56) References Cited

U.S. PATENT DOCUMENTS 4,441,202 A 4/1984 Tong et al.
4,581,491 A * 4/1986 Boothroyd ............ A61F 11/045
340/407.1
(Continued)

FOREIGN PATENT DOCUMENTS

WO 96/12383 * 4/1996 ............. H04R 25/00
WO WO 96/12383 A 4/1996
(Continued)

OTHER PUBLICATIONS

Gadhoumi, K., et al., "A Cochlear Prosthesis Stimulation Algorithm Targeting to Minimize the Rehabilitation Phase And Enhance Speech Comprehension", Engineering in Medicine and Biology Society, 2000, Proceedings of the 22nd Annual International Conference of the IEEE Jul. 23-28, 2000, Chicago, IL, 3 pgs.
(Continued)

*Primary Examiner* — Eric D. Bertram
*Assistant Examiner* — Pamela M. Bays
(74) *Attorney, Agent, or Firm* — Knobbe Martens Olson & Bear LLP

(57) ABSTRACT

Methods and devices to deliver a tactile speech analog to a person's skin providing a silent, invisible, hands-free, eyes-free, and ears-free way to receive and directly comprehend electronic communications. Embodiments include an alternative to hearing aids that will enable people with hearing loss to better understand speech. A device, worn like watch or bracelet, supplements a person's remaining hearing to help identify and disambiguate those sounds he or she can not hear properly. Embodiments for hearing aids and hearing prosthetics are also described.

27 Claims, 17 Drawing Sheets

Related U.S. Application Data

(60) Provisional application No. 60/705,219, filed on Aug. 3, 2005.

(51) Int. Cl.
*H04R 25/00* (2006.01)
*G10L 21/16* (2013.01)
*A61N 1/05* (2006.01)
*G10L 15/02* (2006.01)

(52) U.S. Cl.
CPC .. *G10L 2015/025* (2013.01); *G10L 2021/065* (2013.01); *H04R 25/00* (2013.01); *H04R 25/606* (2013.01)

(58) Field of Classification Search
CPC ...... A61F 11/04; G10L 15/02; G10L 2015/25; G10L 2021/065; G10L 21/06; G10L 21/16
USPC ............ 607/55–57, 136–137; 704/258, 266, 704/270.1
See application file for complete search history.

(56) References Cited

U.S. PATENT DOCUMENTS

| | | | |
|---|---|---|---|
| 4,682,367 A | 7/1987 | Childress et al. | |
| 4,720,848 A | 1/1988 | Akiyama et al. | |
| 5,029,200 A | 7/1991 | Haas et al. | |
| 5,479,489 A | 12/1995 | O'Brien | |
| 5,559,860 A | 9/1996 | Mizikovsky | |
| 5,661,788 A | 8/1997 | Chin | |
| 5,740,532 A | 4/1998 | Fernandez et al. | |
| 5,933,805 A | 8/1999 | Boss et al. | |
| 5,978,689 A | 11/1999 | Tuoriniemi et al. | |
| 5,991,364 A | 11/1999 | McAllister et al. | |
| 5,999,902 A | 12/1999 | Scahill et al. | |
| 6,002,966 A | 12/1999 | Loeb et al. | |
| 6,018,571 A | 1/2000 | Langlois et al. | |
| 6,038,443 A | 3/2000 | Luneau | |
| 6,049,594 A | 4/2000 | Furman et al. | |
| 6,073,094 A | 6/2000 | Chang et al. | |
| 6,088,428 A | 7/2000 | Trandal | |
| 6,122,347 A | 9/2000 | Borland | |
| 6,160,489 A | 12/2000 | Perry et al. | |
| 6,163,691 A | 12/2000 | Buettner et al. | |
| 6,178,167 B1 | 1/2001 | Fraser | |
| 6,289,085 B1 | 9/2001 | Miyashita et al. | |
| 6,319,130 B1 | 11/2001 | Ooseki | |
| 6,353,671 B1* | 3/2002 | Kandel ............... | H04R 25/453 381/312 |
| 6,373,925 B1 | 4/2002 | Guercio et al. | |
| 6,374,217 B1 | 4/2002 | Bellegarda | |
| 6,385,303 B1 | 5/2002 | Peterson et al. | |
| 6,385,584 B1 | 5/2002 | McAllister et al. | |
| 6,421,672 B1 | 7/2002 | McAllister et al. | |
| 6,501,967 B1 | 12/2002 | Mäkelä et al. | |
| 6,573,825 B1 | 6/2003 | Okano | |
| 6,618,474 B1 | 9/2003 | Reese | |
| 6,621,418 B1* | 9/2003 | Cayrol ................... | G01V 3/15 340/4.11 |
| 6,628,195 B1 | 9/2003 | Coudon | |
| 6,636,602 B1 | 10/2003 | Vlacancich | |
| 6,714,637 B1 | 3/2004 | Kredo | |
| 6,807,259 B1 | 10/2004 | Patel et al. | |
| 7,062,036 B2 | 6/2006 | Williams | |
| 7,136,811 B2 | 11/2006 | Tirpak et al. | |
| 7,206,572 B2 | 4/2007 | Luneau | |
| 7,231,019 B2 | 6/2007 | Pascovici | |
| 7,257,210 B1 | 8/2007 | Henderson | |
| 7,260,187 B1 | 8/2007 | McAllister | |
| 7,295,656 B2 | 11/2007 | Ruckart | |
| 7,315,618 B1 | 1/2008 | Moton et al. | |
| 7,366,337 B2 | 4/2008 | Kortum et al. | |
| 7,412,383 B1 | 8/2008 | Alonso et al. | |
| 7,418,096 B2 | 8/2008 | Moton et al. | |
| 7,443,967 B1 | 10/2008 | Silver | |
| 7,483,832 B2 | 1/2009 | Tischer | |
| 7,869,588 B2 | 1/2011 | Fitchmun | |
| 7,881,449 B2 | 2/2011 | Hanson et al. | |
| 7,957,513 B2 | 6/2011 | Bishop | |
| 8,086,245 B2 | 12/2011 | Karaoguz et al. | |
| 8,767,953 B2 | 7/2014 | Fitchmun | |
| 9,544,446 B2 | 1/2017 | Fitchmun | |
| 2002/0094776 A1 | 7/2002 | Pulver | |
| 2002/0118804 A1 | 8/2002 | Carroll | |
| 2002/0137553 A1 | 9/2002 | Kraemer | |
| 2002/0156630 A1 | 10/2002 | Hayashi et al. | |
| 2002/0196914 A1 | 12/2002 | Ruckart | |
| 2003/0013432 A1 | 1/2003 | Fukaya | |
| 2003/0016813 A1 | 1/2003 | Weiner | |
| 2003/0033214 A1 | 2/2003 | Mikkelsen et al. | |
| 2003/0055655 A1 | 3/2003 | Suominen | |
| 2003/0061041 A1 | 3/2003 | Junkins et al. | |
| 2003/0161454 A1 | 8/2003 | Nassimi | |
| 2003/0235282 A1 | 12/2003 | Sichelman | |
| 2004/0037403 A1 | 2/2004 | Koch | |
| 2004/0082980 A1* | 4/2004 | Mouine ............... | A61N 1/36032 607/48 |
| 2004/0114747 A1 | 6/2004 | Trandal et al. | |
| 2004/0233892 A1 | 11/2004 | Roberts et al. | |
| 2005/0243996 A1 | 11/2005 | Fitchmun | |
| 2006/0274144 A1 | 12/2006 | Landschaft et al. | |
| 2007/0147601 A1 | 6/2007 | Tischer | |
| 2009/0024183 A1 | 1/2009 | Fitchmun | |
| 2010/0141467 A1 | 6/2010 | Kirkpatrick | |
| 2010/0219971 A1 | 9/2010 | Appelman et al. | |
| 2011/0123017 A1 | 5/2011 | Fitchmun | |
| 2014/0301544 A1 | 10/2014 | Fitchmun | |
| 2015/0194166 A1 | 7/2015 | Fitchmun | |
| 2017/0149964 A1 | 5/2017 | Fitchmun | |

FOREIGN PATENT DOCUMENTS

| | | |
|---|---|---|
| WO | WO 98/53776 A | 12/1998 |
| WO | WO 99/49681 | 9/1999 |
| WO | WO 2005/109846 A1 | 11/2005 |
| WO | WO 2007/019307 | 2/2007 |

OTHER PUBLICATIONS

International Search Report, Application No. PCT/US2006/030437, dated May 30, 2007, 2 pgs.

International Search Report, Application No. PCT/US2005/014903, dated Sep. 22, 2005, 5 pgs.

\* cited by examiner

Figure 2: English Phonemes

| | Phoneme | | | Example | Articulation | | Features | | |
|---|---|---|---|---|---|---|---|---|---|
| | IPA | s{mpA | m-w | | Manner | Place | Voice | 3kHz+ | Stops |
| 234 | p | p | p | gap | Plosive | Bilabial | | ✓ | ✓ |
| 242 | t | t | t | cat | Plosive | Alveolar | | ✓ | ✓ |
| 243 | k | k | k | cat | Plosive | Velar | | ✓ | ✓ |
| 244 | b | b | b | bad | Plosive | Bilabial | ✓ | ✓ | ✓ |
| 245 | d | d | d | bad | Plosive | Alveolar | ✓ | ✓ | ✓ |
| 250 | g | g | g | gap | Plosive | Velar | ✓ | ✓ | ✓ |
| 252 | tʃ | tS | ch | which | Affricate (Alveolar) | | | ✓ | ✓ |
| 253 | dʒ | dZ | j | joy | Affricate (Alveolar) | | ✓ | ✓ | ✓ |
| 254 | f | f | f | fat | Fricative | Labiodental | | ✓ | |
| 255 | θ | T | th | thing | Fricative | Dental | | ✓ | |
| 261 | s | s | s | shis | Fricative | Aveolar | | ✓ | |
| 264 | ʃ | S | sh | she | Fricative | Palato-alveolar | | ✓ | |
| 267 | h | h | h | hit | Fricative | Aspirate | | ✓ | |
| 274 | v | v | v | love | Fricative | Labiodental | ✓ | ✓ | |
| 275 | ð | D | [th] | this | Fricative | Dental | ✓ | ✓ | |
| 276 | z | z | z | cheese | Fricative | Aveolar | ✓ | ✓ | |
| 271 | ʒ | Z | zh | measure | Fricative | Palato-alveolar | ✓ | ✓ | |
| 280 | m | m | m | mat | Nasal | Bilabial | ✓ | | |
| 281 | n | n | n | nat | Nasal | Alveolar | ✓ | | |
| 282 | ŋ | N | [ng] | thing | Nasal | Velar | ✓ | | |
| 283 | l | l | l | love | Approximant | Lateral | ✓ | | |
| 284 | ɹ | r\ | r | red | Approximant | | ✓ | | |
| 285 | j | j | y | yes | Approximant | Palatal | ✓ | | |
| 286 | w | w | w | which | Approximant | Bilabial | ✓ | | |
| 287 | i | i | E | beet | Monophthong | High Front | ✓ | | |
| 288 | ɪ | I | i | bit | Monophthong | Mid High Front | ✓ | | |
| 289 | ɛ | E | e | bet | Monophthong | Mid Front | ✓ | | |
| 291 | æ | { | a | bat | Monophthong | Mid-Low Front | ✓ | | |
| 292 | ɝ | 3` | &r | hurt | Monophthong | Mid Central (R colored) | ✓ | | |
| 293 | ʌ | V | & | but | Monophthong | Mid Central | ✓ | | |
| 294 | u | u | ü | boot | Monophthong | High Back | ✓ | | |
| 295 | ʊ | U | u | book | Monophthong | High Back | ✓ | | |
| | ɑ | A | ä | cod | Monophthong | Low Back | ✓ | | |
| | ɔ | O | o | bought | Monophthong | Mid Back | ✓ | | |
| | aɪ | e(I) | A | bate | Diphthong | Mid Front → High Front | ✓ | | |
| | eɪ | aI | I | byte | Diphthong | Low Central → High Front | ✓ | | |
| | ɔɪ | oI | oi | joy | Diphthong | Mid Back → Mid Front | ✓ | | |
| | aʊ | aU | au | cow | Diphthong | Low Central → Mid Back | ✓ | | |
| | oʊ | o(U) | O | boat | Diphthong | Mid Back → High Back | ✓ | | |

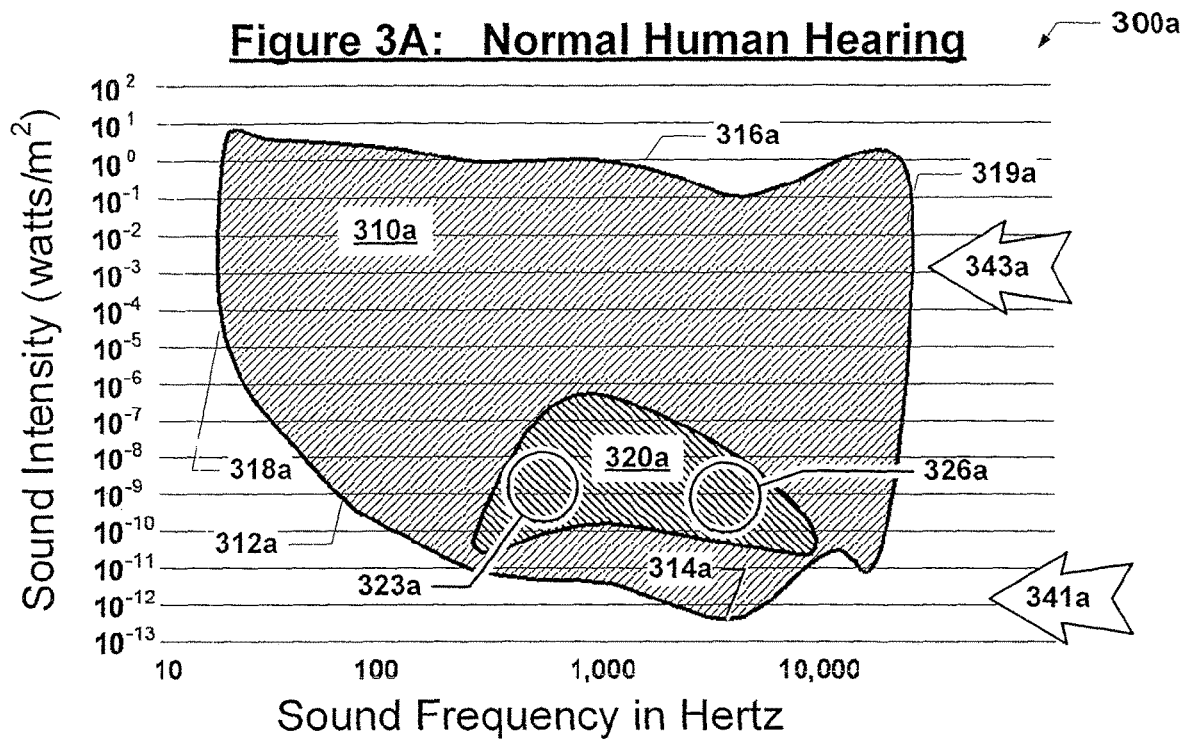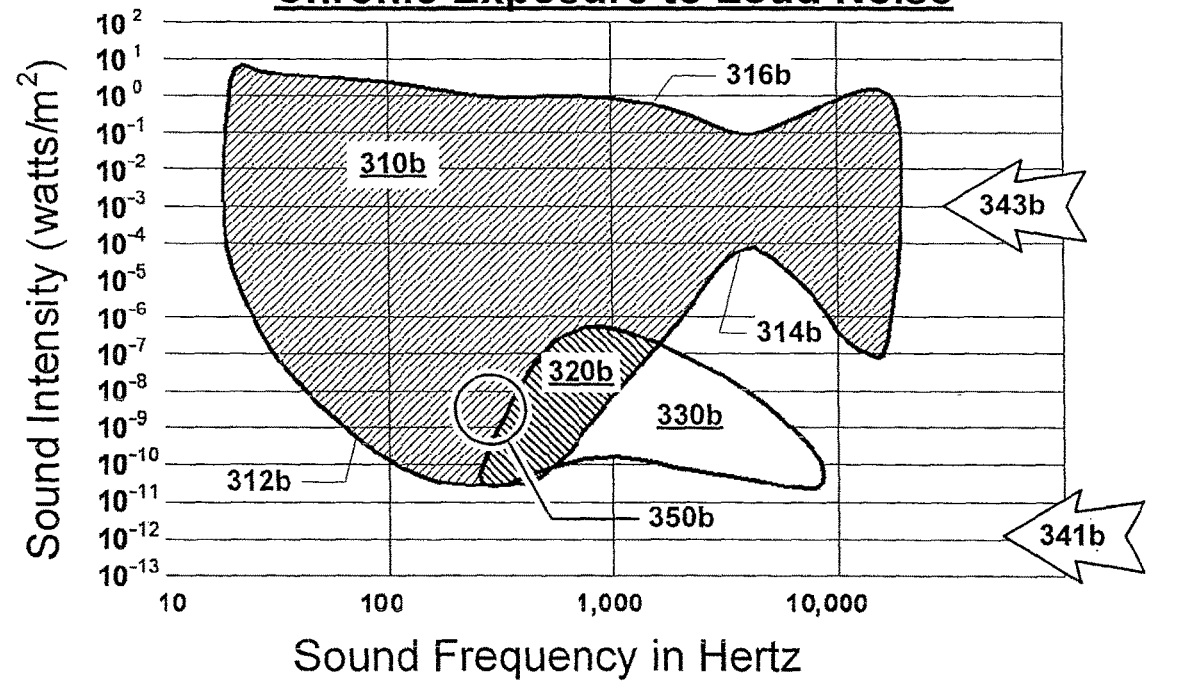

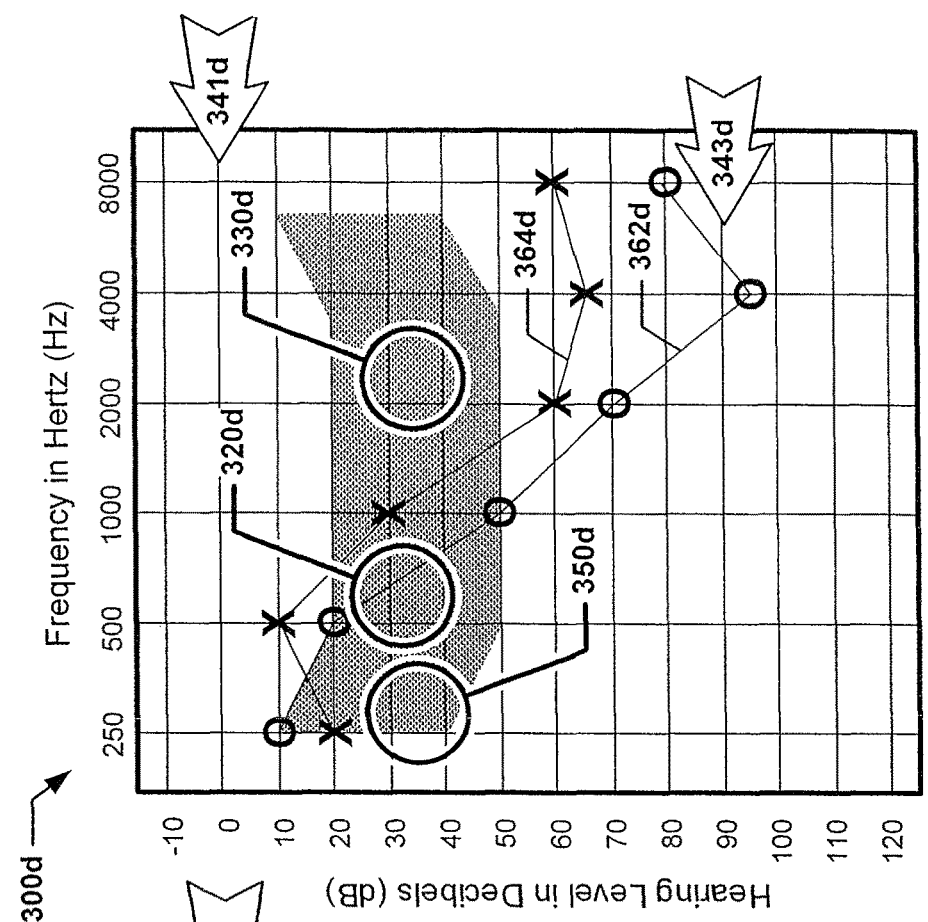
Figure 3C: Normal Human Hearing
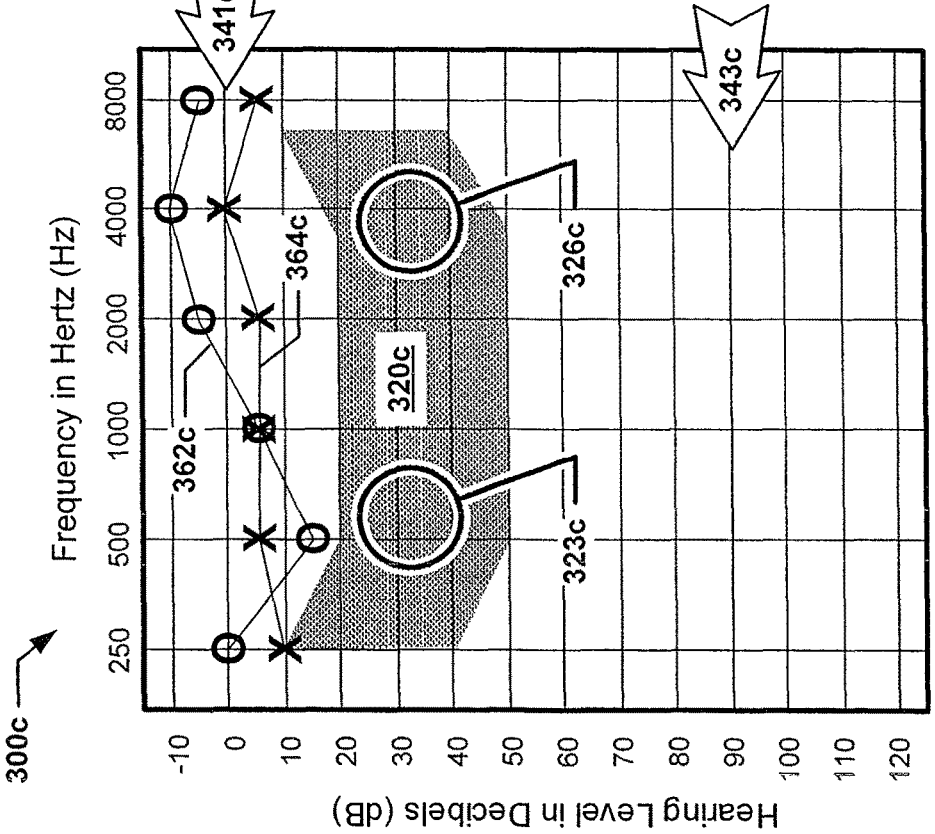
Figure 3D: Hearing Loss Caused by Chronic Exposure to Loud Noise

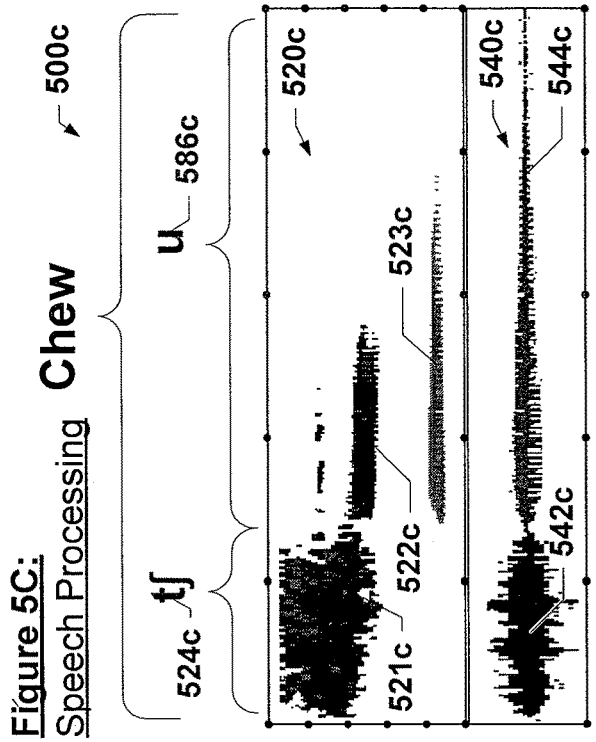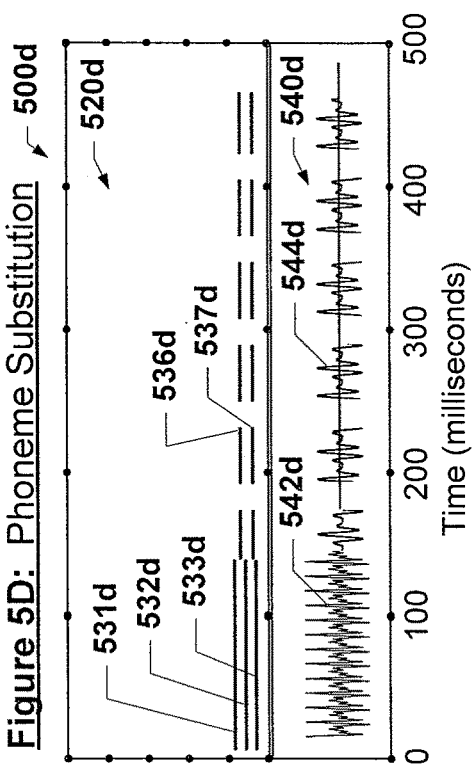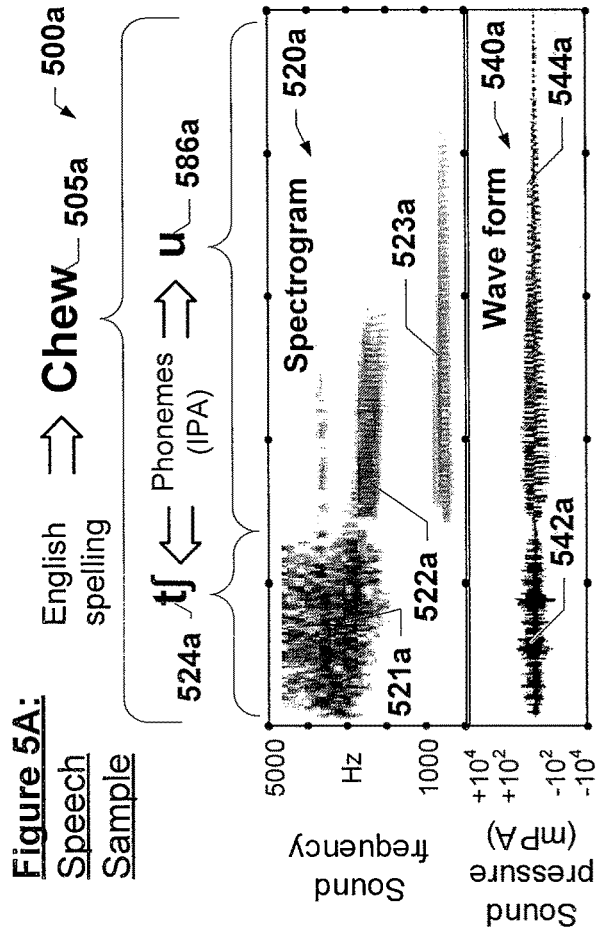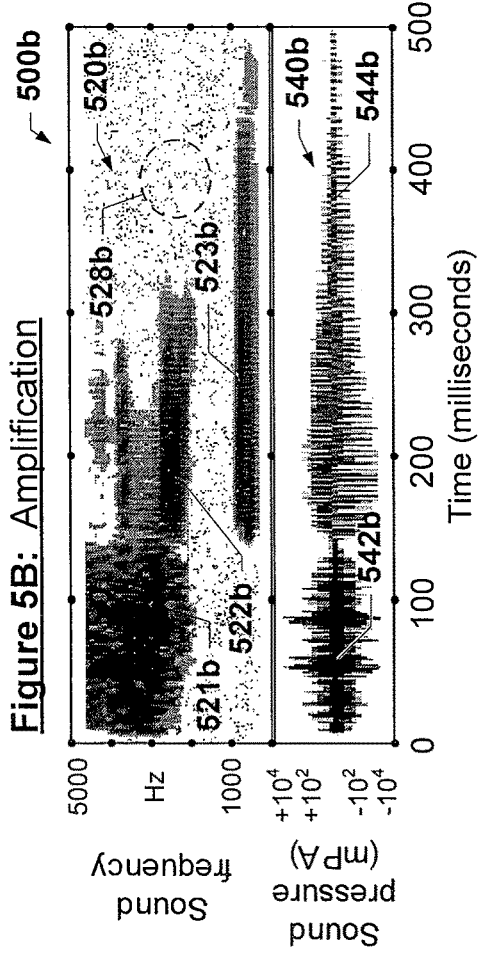

Figure 8: Phoneme Substitution Database

752

801
804
807
811 — (p,(336,20,90,50,0,1,100,100))
814 — (t,(317,20,90,50,-30,1,100,100),(566,20,90,50,-30,1,100,100))
817 — (k,(336,20,90,50,-30,1,100,100),(534,20,90,50,-30,1,100,100))
824 — (b,(336,20,90,50,0,1,100,100),(449,20,90,50,0,1,100,100),(504,20,90,50,0,1,90,50))
834 — (d,(336,20,90,50,0,1,100,100),(424,20,90,50,0,1,100,100),(504,20,90,50,0,1,90,50))
842 — (g,(336,20,90,50,0,1,100,100),(504,20,90,50,0,1,90,50))
843 — (tʃ,(317,20,90,50,0,1,100,100),(449,20,90,50,0,1,100,100),(566,20,90,50,0,1,100,100))
844 — (dʒ,(449,20,90,50,0,1,100,100),(504,20,90,50,0,1,90,50))
845 — (f,(400,0,100,50,0,1,100,100),(566,0,100,40,20,1,100,100))
850 — (θ,(424,0,100,50,0,1,100,100),(566,0,100,50,0,1,100,100))
852 — (s,(534,0,100,50,0,1,100,100),(566,0,100,50,0,1,100,100))
853 — (ʃ,(449,0,100,40,20,1,100,100),(566,0,100,50,0,1,100,100))
854 — (h,(449,0,100,30,20,1,100,100))
855 — (v,(300,0,100,50,0,1,100,100),(504,0,100,40,30,1,85,50))
861 — (ð,(300,0,100,50,0,1,100,100),(449,0,100,50,0,1,100,100),(504,10,100,60,0,1,75,30))
864 — (z,(300,0,100,50,0,1,100,100),(424,0,100,50,0,1,100,100),(504,0,100,60,0,1,65,30))
867 — (ʒ,(300,0,100,50,0,1,100,100),(400,0,100,50,0,1,100,100),(504,-5,100,60,0,1,55,30))
874 — (m,(336,0,100,50,0,1,100,100),(400,0,100,50,0,1,100,100),(534,0,100,60,0,1,126,80))
875 — (n,(336,0,100,50,0,1,100,100),(424,0,100,50,0,1,100,100),(534,0,100,60,0,1,126,80))
876 — (ŋ,(336,0,100,50,0,1,100,100),(449,0,100,50,0,1,100,100),(534,0,100,60,0,1,126,80))
871 — (l,(300,0,100,50,0,1,133,85),(423,0,100,55,0,1,133,85))
880 — (ɹ,(300,0,100,55,0,1,94,75),(336,0,100,50,0,1,94,75))
881 — (j,(300,0,100,50,0,1,100,100),(449,0,100,50,0,1,150,83))
882 — (w,(300,0,100,60,0,1,84,70))
883 — (i,(336,0,100,50,0,1,100,67),(566,0,100,50,0,1,100,67))
884 — (ɪ,(424,0,100,50,0,1,100,67),(534,0,100,50,0,1,100,67))
885 — (ɛ,(400,0,100,50,0,1,100,67),(534,0,100,50,0,1,100,67))
886 — (æ,(300,0,100,50,0,1,100,67),(534,,0,100,50,0,1,100,67))
887 — (ɜ,(300,0,100,55,0,1,94,75),(336,0,100,50,0,1,94,75))
888 — (ʌ,(424,0,100,50,0,1,100,67))
889 — (u,(400,0,150,50,0,1,100,67),(504,0,150,50,0,1,100,67))
891 — (ʊ,(336,0,100,50,0,1,100,67),(400,0,100,50,0,1,100,67))
892 — (ɑ,(317,0,100,50,0,1,100,67),(449,0,100,50,0,1,100,67))
893 — (ɔ,(317,0,100,50,0,1,100,67),(424,0,100,50,0,1,100,67))
894 — (aɪ,(336,0,150,50,0,1,100,67),(424,0,150,50,0,1.25,100,67),(556,0,150,50,0,1,100,67))
895 — (eɪ,(336,0,150,50,0,1,100,67),(449,0,150,50,0,1.12,100,67),(556,0,150,50,0,0.9,100,67))
(ɔɪ,(336,0,150,50,0,1,100,67),(400,0,150, 50,0,1.4,100,67),(556,0,150,50,0,1,100,67))
(aʊ,(317,0,150,50,0,1,84,67),(400,0,150,50,0,0.75,84,67))
(oʊ,(424,0,100,50,0,1.09,100,67),(504,0,100,50,0,0.92,100,67))

Cochlear Implants

Implant Output Signal Comparison

Speech Example

1100a

Conventional Sound Processing

1100b

Phoneme Substitution

1100c

Figure 13: Electrode Assignments
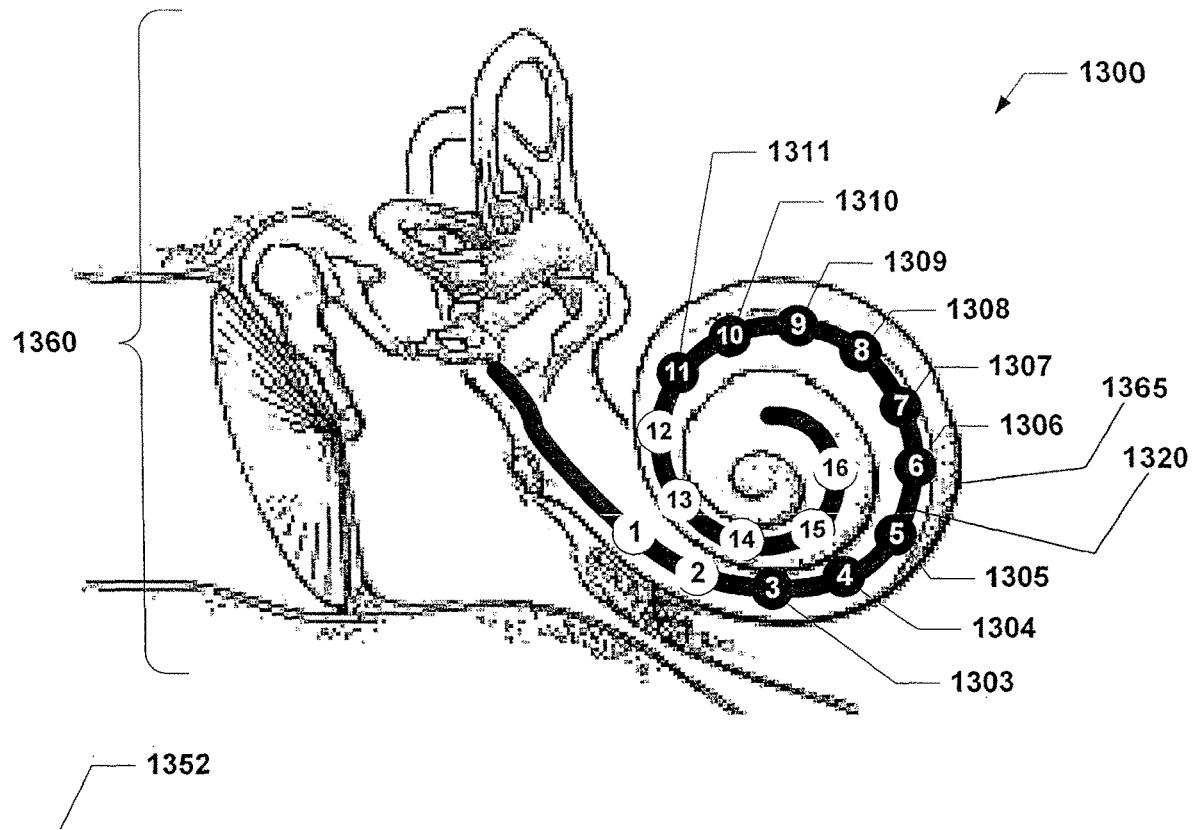
| Phoneme | Channel Assignment | Phoneme | Channel Assignment | Phoneme | Channel Assignment |
|---|---|---|---|---|---|
| p | 5 | h | 8 | ɛ | 6, 10 |
| t | 4, 11 | v | 3, 9 | æ | 3, 10 |
| k | 5, 10 | ð | 3, 8, 9 | u | 6, 9 |
| b | 5, 8, 9 | z | 3, 7, 9 | ʊ | 6 |
| d | 5, 7, 9 | ʒ | 3, 6, 9 | ʌ | 7 |
| g | 5, 9 | l | 3, 7 | ɑ | 4, 8 |
| m | 5, 6, 10 | ɹ | 3, 5 | ɔ | 4, 7 |
| n | 5, 7, 10 | j | 3, 8 | aɪ | 5, 7, 11 |
| ŋ | 5, 8, 10 | w | 1 | eɪ | 5, 8, 11 |
| f | 6, 11 | tʃ | 4, 8, 11 | ɔɪ | 5, 6, 11 |
| θ | 7, 11 | dʒ | 8, 9 | aʊ | 4, 6 |
| s | 11 | i | 5, 11 | oʊ | 7, 9 |
| ʃ | 8, 11 | ɪ | 7, 10 | ɜ | 3, 5 |

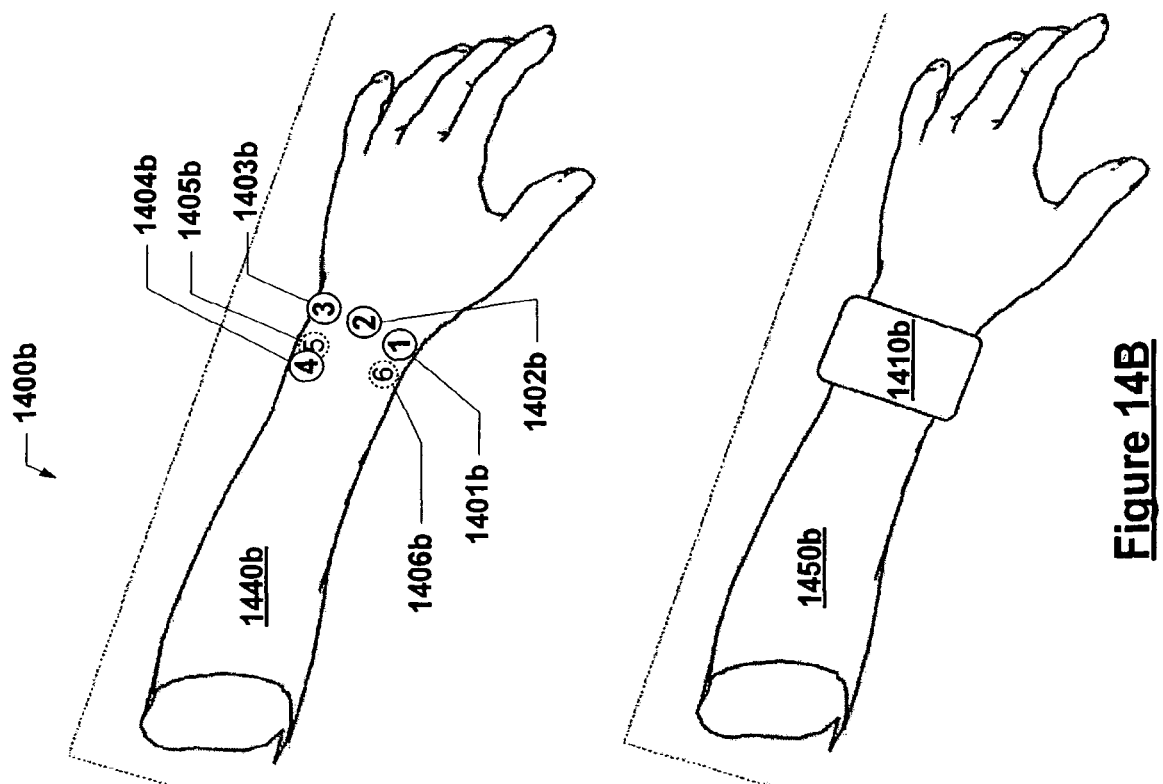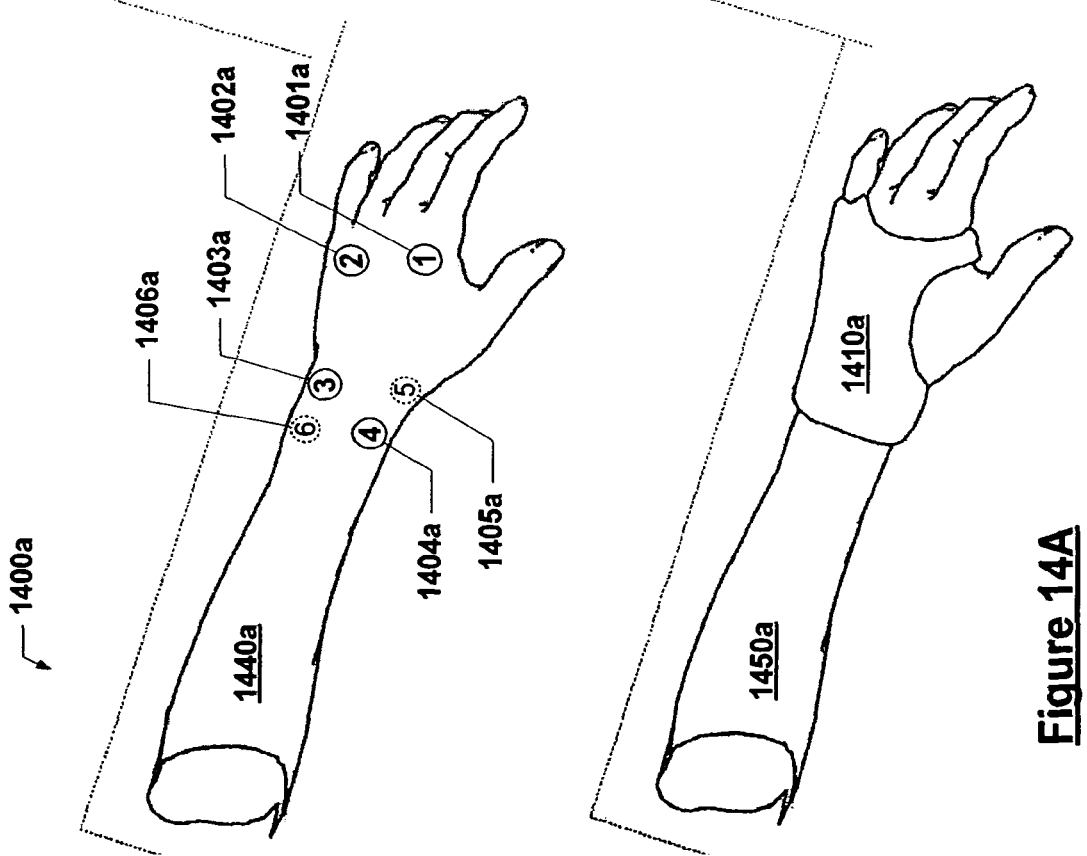
Figure 14B
Figure 14A

Figure 15

| Phoneme IPA Symbol | Channel Assignments | | |
|---|---|---|---|
| | Example 1 | Example 2 | Example 3 |
| p | 1, 2, 5 | [1], 2, 5 | [1], 2, [5] |
| t | 1 | [1] | [1] |
| k | 1, 2, 3 | [1], 2, 3 | [1], 2, [3] |
| b | 1, 2, 3, 6 | [1], 2, 3, 6 | [1], 2, [3], 6 |
| d | 1, 2 | [1], 2 | [1], 2 |
| g | 1, 2, 3, 4, 5 | [1], 2, 3, 4, 5 | [1], 2, [3], 4, [5] |
| m | 2, 4 | [2], 4 | 2, 4 |
| n | 2 | [2] | 2 |
| ŋ | 2, 6 | [2], 6 | 2, 6 |
| f | 3, 4, 5 | [3], 4, 5 | [3], 4, [5] |
| θ | 1, 3 | 1, [3] | [1], [3] |
| s | 3 | [3] | [3] |
| ʃ | 2, 3, 4 | 2, [3], 4 | 2, [3], 4 |
| h | 2, 3, 5 | 2, [3], 5 | 2, [3], [5] |
| v | 2, 3, 4, 5 | 2, [3], 4, 5 | 2, [3], 4, [5] |
| ð | 1, 3, 4, 5 | 1, [3], 4, 5 | [1], [3], 4, [5] |
| z | 3, 4 | [3], 4 | [3], 4 |
| ʒ | 1, 2, 3, 4, 5, 6 | 1, 2, [3], [4], 5, 6 | [1], 2, [3], 4, [5], 6 |
| l | 4, 5 | [4], 5 | 4, [5] |
| ɹ | 4 | [4] | 4 |
| j | 1, 2, 4, 6 | 1, 2, [4], 6 | [1], 2, 4, 6 |
| w | 4, 5, 6 | [4], 5, 6 | 4, [5], 6 |
| tʃ | 1, 2, 3, 4 | [1], 2, [3], 4 | [1], 2, [3], 4 |
| dʒ | 1, 3, 4, 5, 6 | [1], [3], 4, 5, 6 | [1], [3], 4, [5], 6 |
| i | 1, 2, 6 | 1, 2, [6] | [1], 2, 6 |
| ɪ | 5, 6 | [5], 6 | [5], 6 |
| ɛ | 2, 5 | 2, [5] | 2, [5] |
| æ | 1, 5, 6 | 1, [5], 6 | [1], [5], 6 |
| u | 1, 4, 5 | 1, 4, [5] | [1], 4, [5] |
| ʊ | 2, 4, 5 | 2, 4, [5] | 2, 4, [5] |
| ʌ | 5 | [5] | [5] |
| ɑ | 1, 2, 4, 5 | 1, 2, 4, [5] | [1], 2, 4, [5] |
| ɔ | 2, 4, 5, 6 | 2, 4, [5], 6 | 2, 4, [5], 6 |
| aɪ | 1, 6 | 1, [6] | [1], 6 |
| eɪ | 6 | [6] | 6 |
| ɔɪ | 1, 2, 3, 4, 6 | 1, 2, 3, 4, [6] | [1], 2, [3], 4, 6 |
| aʊ | 1, 4, 6 | 1, 4, [6] | [1], 4, 6 |
| oʊ | 4, 6 | 4, [6] | 4, 6 |
| ɝ | 4 | [4] | 4 |

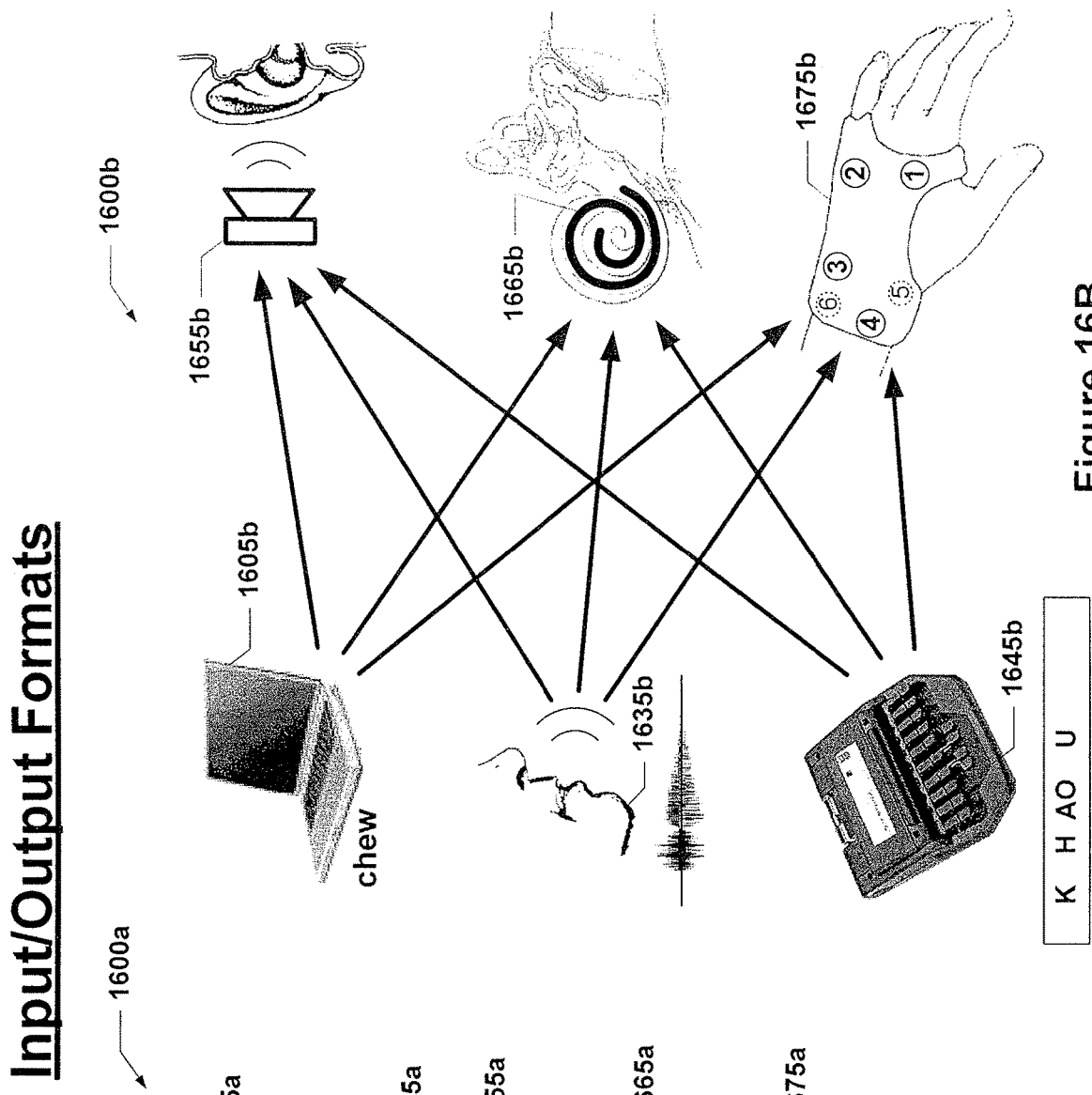
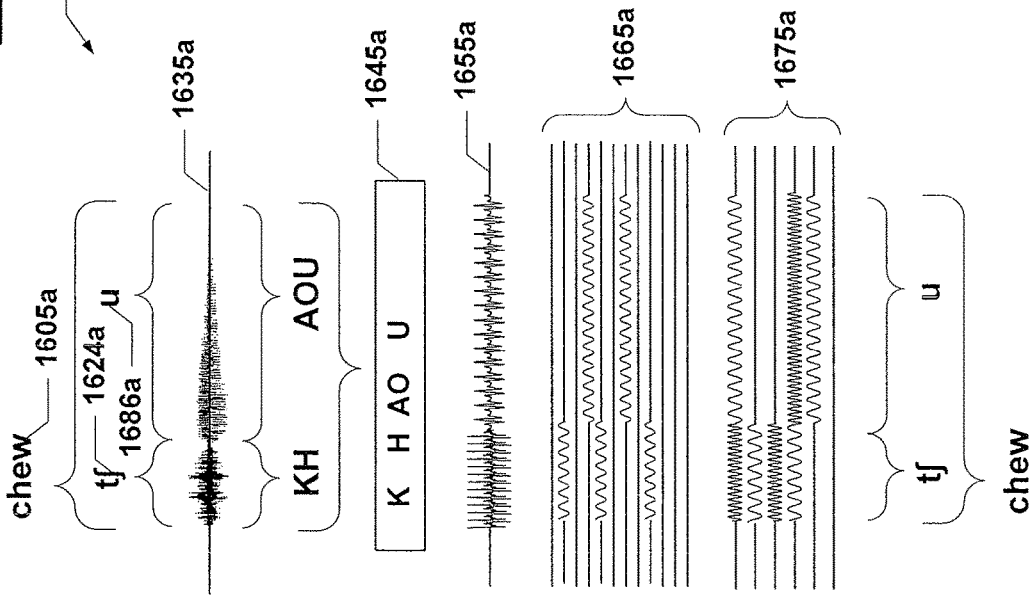
Figure 16A
Figure 16B
Input/Output Formats

SOMATIC, AUDITORY AND COCHLEAR COMMUNICATION SYSTEM AND METHOD

REFERENCE TO PRIOR APPLICATION

This application is a continuation of U.S. application Ser. No. 11/997,902, having a 371 date of Sep. 8, 2008, which was the National Stage application of and claims benefit of priority to International Application No. PCT/US2006/030437, filed on Aug. 3, 2006, which claims the benefit of priority to U.S. Provisional Application No. 60/705,219, filed on Aug. 3, 2005. The disclosures of each of the above-described applications are hereby expressly incorporated by reference in their entirety.

BACKGROUND

Field of the Invention

The invention relates to somatic, auditory or cochlear communication to a user, and more particularly, to somatic, auditory or cochlear communication using phonemes.

Description of the Related Art

Phonemes are the speech sounds that form the words of a language, when used alone or when combined. More precisely, a phoneme is the smallest phonetic unit, or part of speech that distinguishes one word from another. Various nomenclatures have been developed to describe words in terms of their constituent phonemes. The nomenclature of the International Phonetic Association (IPA) will be used here. Unless otherwise noted, examples of speech, speech sounds, phonetic symbols, phonetic spellings, and conventional spellings will be with respect to an American dialect of English, hereto forth referred to simply as English. The principles can be extended to other languages.

FIG. 1 illustrates several exemplary plots 100 to introduce several spectral and temporal features of human speech through the examination of the English word, "fake", 105, and its component phonemes. The phonetic spelling (per the IPA) of the English word, "fake", 105, is "faik", 110. In English, the word comprises three separate phonemes: the consonant, "f", 142; the diphthong vowel, "ai", 191; and the consonant, "k", 107. Because phonemes are language and dialect dependent, an English speaker will hear "ai" as a single sound, "long A", 191, a diphthong (a sound combining two vowel sounds), while speakers of other languages may hear two different vowels, "a", 113, and "i", 114, each a monophthong (a single vowel sound). The phoneme, "k", 107, also comprises two parts: a short period of relative silence, 117; followed by the abrupt appearance of sound frequencies in a range of about 2500 to 7000 Hz, 118.

Spectral and temporal features of the individual phonemes are partially observable when viewing a plot of the waveform 140 of the spoken word. Here, pressure is shown on the vertical axis and time is shown on the horizontal axis. A spectrogram 120 reveals greater detail and structure. Here, frequency is shown on the vertical axis, time on the horizontal axis, and power is represented as a grey scale, with darker shades corresponding to higher power (sound intensity) levels. The consonants "f", 142, and "k", 107, primarily consist of sound frequencies above approximately 3000 Hz, while the vowel "ai", 191, primarily consists of sound frequencies below approximately 3500 Hz. The highlighted areas of the spectrogram 132, 134, 138 reveal additional features of human speech.

An early portion of the phoneme "f", 132, magnified in panel (A), 133, comprises sound frequencies predominantly above 3000 Hz. The distribution of power is irregular over time and frequency giving rise to a sound quality resembling rushing air, and creating the granular pattern on the spectrogram 132, 133.

The highlighted portion of the phoneme "ai", 134, magnified in panel (B), 135, shows a bimodal distribution of relatively low sound frequencies. Characteristic of diphthongs, one or more dominant frequencies, called "formants", shift in frequency over time. A portion 136 of panel (B), 135, magnified further in panel (D), 137, reveals a waxing and waning of power in all frequencies, a characteristic of the human voice. Unvoiced phonemes such as "f", 142, 132, 133, and "k", 107, 118, 138, 139, do not exhibit these cyclical amplitude fluctuations.

Some phonemes increase or decrease in power or intensity over their duration. This is evident in the highlighted portion of the phoneme "k", 138, magnified in panel (C), 139. Here, sound energy decreases continually during a period of about 70 milliseconds.

Another important feature of human speech is the period of relative silence preceding some consonants. In the current example, the phoneme 'k", 107, comprises approximately 70 milliseconds of quiet 117 followed by the audible portion 118 of the phoneme "k", 107. Without this period of relative silence, some phonemes, including "k" would be unintelligible. Also, intervals of relative silence or power shifts are important for syllabification.

FIG. 2 is a table 200 of American English phonemes 225 shown in three nomenclatures: the International Phonics Association (IPA), s{mpA (a phonetic spelling of SAMPA, the abbreviation for Speech Assessment Methods Phonetic Alphabet, a computer readable phonetic alphabet), and the Merriam Webster Online Dictionary (m-w). Examples 226 of each phoneme (bold underlined letters) as used in an American English word are provided, along with the manner 237 and place 247 of articulation 227.

The manner of articulation 237 refers primarily to the way in which the speech organs, such as the vocal cords, tongue, teeth, lips, nasal cavity, etc. are used. Plosives 201, 204, 207, 211, 214, 217 are consonants pronounced by completely closing the breath passage and then releasing air. Fricatives 242, 243, 244, 245, 250, 252, 253, 254, 255 are consonants pronounced by forcing the breath through a narrow opening. Between the plosives, and the fricatives are two affricates 224, 234 composite speech sounds that begin as a plosive and end as a fricative. Nasals 261, 264, 267 are consonants pronounced with breath escaping mainly through the nose rather than the mouth. Approximants 274, 275, 276, 271 are sounds produced while the airstream is barely disturbed by the tongue, lips, or other vocal organs. Vowels are speech sounds produced by the passage of air through the vocal tract, with relatively little obstruction, including the monophthong vowels 280, 281, 282, 283, 284, 285, 286, 287, 288, 289 and the diphthong vowels 291, 292, 293, 294, 295.

The place of articulation 247 refers largely to the position of the tongue, teeth, and lips. Bilabials, are pronounced by bringing both lips into contact with each other or by rounding them. Labiodentals are pronounced with the upper teeth resting on the inside of the lower lip. Dentals are formed by placing the tongue against the back of the top front teeth. Alveolars are sounded with the tongue touching or close to the ridge behind the teeth of the upper jaw. Palato-alveolars are produced by raising the tongue to or near the forwardmost portion of the hard palate. Palatals are produced by raising the tongue to or near the hard palate. Velars are spoken with the back of the tongue close to, or in contact with, the soft palate (velum).

Other speech characteristics 228 include voice, dominant sound frequencies above about 3000 Hz (3 kHz+), and stops. In English, eight phonemes comprise a period of relative silence followed by a period of relatively high sound energy. These phonemes, called stops 228 are the plosives and the affricates 201, 204, 207, 211, 214, 217, 224, 234. Stops are not recognizable from their audible portion alone. Recognition of these phonemes requires that they begin with silence. Phonemes may be voiced or unvoiced. For example, "b", 211, is the voiced version of "p", 201, and "z", 254, is the voiced version of "s", 244. Most English consonants, the plosives, affricates, and fricatives 201, 204, 207, 211, 214, 217, 224, 234, 242, 243, 244, 245, 250, 252, 253, 254, 255 comprise sound frequencies above 3000 Hz. In order for an individual to be able to discriminate between these phonemes, he/she must be able to hear their higher frequencies. Unvoiced phonemes 201, 204, 207, 224, 242, 243, 244, 245, 250 in particular tend to be dominated by the higher sound frequencies.

SUMMARY OF CERTAIN EMBODIMENTS

In another embodiment there is a method of transforming a sequence of symbols representing phonemes into a sequence of arrays of nerve stimuli, the method comprising establishing a correlation between each member of a phoneme symbol set and an assignment of one or more channels of a multi-electrode array, accessing a sequence of phonetic symbols corresponding to a message, and activating a sequence of one or more electrodes corresponding to each phonetic symbol of the message identified by the correlation. The phonetic symbols may belong to one of SAMPA, Kirshenbaum, or IPA Unicode digital character sets. The symbols may belong to the cmudict phoneme set. The correlation may be a one to one correlation. Activating a sequence of one or more electrodes may include an energizing period for each electrode, wherein the energizing period comprises a begin time parameter and an end time parameter. The begin time parameter may be representative of a time from an end of components of a previous energizing period of a particular electrode. The electrodes may be associated with a hearing prosthesis. The hearing prosthesis may comprise a cochlear implant.

In one embodiment there is a method of processing a sequence of spoken words into a sequence of sounds, the method comprising converting a sequence of spoken words into electrical signals, digitizing the electrical signals representative of the speech sounds, transforming the speech sounds into digital symbols representing corresponding phonemes, transforming the symbols representing the corresponding phonemes into sound representations, and transforming the sound representations into sounds.

Transforming the symbols representing the phonemes into sound representations may comprise accessing a data structure configured to map phonemes to sound representations, locating the symbols representing the corresponding phonemes in the data structure, and mapping the phonemes to sound representations. The method additionally may comprise creating the data structure, comprising identifying phonemes corresponding to a language used by a user of the method, establishing a set of allowed sound frequencies, generating a correspondence mapping the identified phonemes to the set of allowed sound frequencies such that each constituent phoneme of the identified phonemes is assigned a subset of one or more frequencies from the set of allowed sound frequencies, and mapping each constituent phoneme of the identified phonemes to a set of one or more sounds. Establishing a set of allowed sound frequencies may comprise selecting a set of sound frequencies that are in a hearing range of the user. Each sound of the set of one more sounds may comprise an initial frequency parameter. Each sound of the set of one more sounds may comprise a begin time parameter. The begin time parameter may be representative of a time from an end of components of a previous sound representation. Each sound of the set of one more sounds may comprise an end time parameter. Each sound of the set of one more sounds may comprise a power parameter. Each sound of the set of one more sounds may comprise a power shift parameter. Each sound of the set of one more sounds may comprise a frequency shift parameter. Each sound of the set of one more sounds may comprise a pulse rate parameter. Each sound of the set of one more sounds may comprise a duty cycle parameter.

In another embodiment there is a method of processing a sequence of spoken words into a sequence of nerve stimuli, the method comprising converting a sequence of spoken words into electrical signals, digitizing the electrical signals representative of the speech sounds, transforming the speech sounds into digital symbols representing corresponding phonemes, transforming the symbols representing the corresponding phonemes into stimulus definitions and transforming the stimulus definitions into a sequence of nerve stimuli.

The nerve stimuli may be associated with a hearing prosthesis. The hearing prosthesis may comprise a cochlear implant. The nerve stimuli may be associated with a skin interface. The skin interface may be located on the wrist and/or hand of the user. Alternatively, the skin interface may be located on the ankle and/or foot of the user. The nerve stimuli may be mechanical and/or electrical. Transforming the symbols representing the phonemes into stimulus definitions may comprise accessing a data structure configured to map phonemes to stimulus definitions, locating the symbols representing the corresponding phonemes in the data structure, and mapping the phonemes to stimulus definitions. The stimulus definitions may comprise sets of one or more stimuli. The sets of one or more stimuli may correspond to one or more locations on the skin or one or more locations in the cochlea. Each stimulus of the sets of one or more stimuli may comprise a begin time parameter. The begin time parameter may be representative of a time from an end of components of a previous stimulus definition. Each stimulus of the sets of one or more stimuli may comprise an end time parameter.

In another embodiment there is a method of transforming a sequence of symbols representing phonemes into a sequence of arrays of nerve stimuli, the method comprising establishing a correlation between each member of a phoneme symbol set and an assignment of one or more channels of a multi-stimulator array, accessing a sequence of phonetic symbols corresponding to a message, and activating a sequence of one or more stimulators corresponding to each phonetic symbol of the message identified by the correlation. The stimulators may be vibrators affixed to the user's skin. The phonetic symbols may belong to one of SAMPA, Kirshenbaum, or IPA Unicode digital character sets. The symbols may belong to the cmudict phoneme set. The correlation may be a one to one correlation. Activating a sequence of one or more stimulators may include an energizing period for each stimulator, wherein the energizing period comprises a begin time parameter and an end time parameter. The begin time parameter may be representative of a time from an end of components of a previous energizing period of a particular stimulator.

In another embodiment there is a method of training a user, the method comprising providing a set of somatic stimulations to a user, wherein the set of somatic stimulations is indicative of a plurality of phonemes, and wherein the phonemes are based at least in part on an audio communication; providing the audio communication concurrently to the user with the plurality of phonemes; and selectively modifying at least portions of the audio communication to the user during the providing of the set of somatic stimulations to the user.

Selectively modifying at least portions of the audio communication may comprise reducing an audio property of the audio communication. The audio property may comprise a volume of the audio. The audio property may comprise omitting selected words from the audio. The audio property may comprise attenuating a volume of selected words from the audio. The audio property may comprise omitting selected phonemes from the audio. The audio property may comprise attenuating a volume of selected phonemes from the audio. The audio property may comprise omitting selected sound frequencies from the audio. The audio property may comprise attenuating a volume of selected sound frequencies from the audio.

In another embodiment there is a method of training a user, the method comprising providing a set of somatic stimulations to a user, wherein the set of somatic stimulations is indicative of a plurality of phonemes, and wherein the phonemes are based at least in part on an audiovisual communication; providing the audiovisual communication concurrently to the user with the plurality of phonemes; and selectively modifying at least portions of the audiovisual communication to the user during the providing of the set of somatic stimulations to the user.

Selectively modifying at least portions of the audiovisual communication may comprise reducing an audio or video property of the audiovisual communication. The audio property may comprise a volume of the audio. The audio property may comprise omitting selected words from the audio. The audio property may comprise attenuating a volume of selected words from the audio. The audio property may comprise omitting selected phonemes from the audio. The audio property may comprise attenuating a volume of selected phonemes from the audio. The audio property may comprise omitting selected sound frequencies from the audio. The audio property may comprise attenuating a volume of selected sound frequencies from the audio. The video property may comprise a presence or brightness of the video.

In another embodiment there is a system for processing a sequence of spoken words into a sequence of sounds, the system comprising a first converter configured to digitize electrical signals representative of a sequence of spoken words, a speech recognizer configured to receive the digitized electrical signals and generate a sequence of phonemes representative of the sequence of spoken words, a mapper configured to assign sound sets to phonemes utilizing an audiogram so as to generate a map, a transformer configured to receive the sequence of phonemes representative of the sequence of spoken words and the map and to generate a sequence of sound representations corresponding to the sequence of phonemes, and a second converter configured to convert the sequence of sound representations into a sequence of audible sounds. The map may be a user-specific map based on a particular user's audiogram.

In another embodiment there is a system for processing a sequence of spoken words into a sequence of sounds, the system comprising a first converter configured to digitize electrical signals representative of a sequence of spoken words, a speech recognizer configured to receive the digitized electrical signals and generate a sequence of phonemes representative of the sequence of spoken words, a data structure comprising sound sets mapped to phonemes, a transformer configured to receive the sequence of phonemes representative of the sequence of spoken words and the data structure and to generate a sequence of sound representations corresponding to the sequence of phonemes, and a second converter configured to convert the sequence of sound representations into a sequence of audible sounds. The data structure may be generated utilizing a user's audiogram.

In another embodiment there is a system for processing a sequence of spoken words into a sequence of nerve stimuli, the system comprising a converter configured to digitize electrical signals representative of a sequence of spoken words, a speech recognizer configured to receive the digitized electrical signals and generate a sequence of phonemes representative of the sequence of spoken words, a mapper configured to assign nerve stimuli arrays to phonemes utilizing an audiogram so as to generate a map, and a transformer configured to receive the sequence of phonemes representative of the sequence of spoken words and the map and to generate a sequence of stimulus definitions corresponding to the sequence of phonemes. The system may additionally comprise a receiver configured to convert the sequence of stimulus definitions into electrical waveforms and an electrode array configured to receive the electrical waveforms. The electrode array may be surgically placed in the user's cochlea. The sequence of stimulus definitions may comprise digital representations of nerve stimulation patterns.

In another embodiment there is a system for processing a sequence of spoken words into a sequence of nerve stimuli, the system comprising a converter configured to digitize electrical signals representative of a sequence of spoken words, a speech recognizer configured to receive the digitized electrical signals and generate a sequence of phonemes representative of the sequence of spoken words, a data structure comprising nerve stimuli arrays mapped to phonemes, and a transformer configured to receive the sequence of phonemes representative of the sequence of spoken words and the data structure and to generate a sequence of stimulus definitions corresponding to the sequence of phonemes. The data structure may be generated utilizing a user's audiogram. The system may additionally comprise a receiver configured to convert the sequence of stimulus definitions into electrical waveforms and an electrode array configured to receive the electrical waveforms. The electrode array may be surgically placed in the user's cochlea. The sequence of stimulus definitions may comprise digital representations of nerve stimulation patterns.

In another embodiment there is a system for processing a sequence of spoken words into a sequence of nerve stimuli, the system comprising a processor configured to generate a sequence of phonemes representative of a sequence of spoken words and to transform the sequence of phonemes using a data structure comprising nerve stimuli arrays mapped to phonemes to produce a sequence of stimulus definitions corresponding to the sequence of phonemes, and an electrode array configured to play the sequence of stimulus definitions. The data structure may be generated utilizing a user's audiogram. The electrode array may comprise a converter configured to convert the sequence of stimulus definitions into electrical waveforms. The electrode array may be surgically placed in the user's cochlea. The electrode array may comprise a plurality of mechanical stimulators or a plurality of electrodes. The sequence of stimulus definitions may comprise digital representations of nerve stimulation patterns.

In another embodiment there is a system for processing a sequence of spoken words into a sequence of sounds, the system comprising a processor configured to generate a sequence of phonemes representative of the sequence of spoken words and to transform the sequence of phonemes using a data structure comprising sound sets mapped to phonemes to produce sound representations corresponding to the sequence of phonemes, and a converter configured to convert the sound representations into audible sounds. The data structure may be generated utilizing a user's audiogram.

In another embodiment there is a system for processing a sequence of text into a sequence of sounds, the system comprising, a first converter configured to receive a sequence of text and generate a sequence of phonemes representative of the sequence of text, a mapper configured to assign sound sets to phonemes utilizing a hearing audiogram so as to generate a map, a transformer configured to receive the sequence of phonemes representative of the sequence of text and the map and to generate sound representations corresponding to the sequence of phonemes, and a second converter configured to convert the sound representations into audible sounds. The hearing audiogram may be representative of a normal human hearing range. The hearing audiogram may be representative of a hearing range for a specific individual.

In another embodiment there is a system for processing a sequence of text into a sequence of sounds, the system comprising a text converter configured to receive a sequence of text and generate a sequence of phonemes representative of the sequence of text, a data structure comprising sound sets mapped to phonemes, a transformer configured to receive the sequence of phonemes representative of the sequence of text and the data structure and to generate sound representations corresponding to the sequence of phonemes, and a second converter configured to convert the sound representations into audible sounds. The data structure may be generated utilizing a user's audiogram.

In another embodiment there is a system for processing a sequence of text into a sequence of nerve stimuli, the system comprising a converter configured to receive a sequence of text and generate a sequence of phonemes representative of the sequence of text, a data structure comprising nerve stimuli arrays mapped to phonemes, and a transformer configured to receive the sequence of phonemes representative of the sequence of text and the data structure and to generate a sequence of stimulus definitions corresponding to the sequence of phonemes. The data structure may be generated utilizing a user's abilities. The user's abilities may comprise useable channels of a cochlear implant of the user. The user's abilities may comprise the ability to distinguish between two or more unique stimuli.

In another embodiment there is a method of processing a sequence of text into a sequence of sounds, the method comprising transforming the sequence of text into digital symbols representing corresponding phonemes, transforming the symbols representing the corresponding phonemes into sound representations, and transforming the sound representations into a sequence of sounds.

In another embodiment there is a method of processing a sequence of text into a sequence of nerve stimuli, the method comprising transforming the sequence of text into digital symbols representing corresponding phonemes, transforming the symbols representing the corresponding phonemes into stimulus definitions, and transforming the stimulus definitions into a sequence of nerve stimuli. The nerve stimuli may be associated with a cochlear implant. The nerve stimuli may be associated with a skin interface, where the skin interface may be located on the wrist and/or hand of the user. Transforming the symbols representing the phonemes into stimulus definitions may comprise accessing a data structure configured to map phonemes to stimulus definitions, locating the symbols representing the corresponding phonemes in the data structure, and mapping the phonemes to stimulus definitions.

In yet another embodiment there is a method of creating a data structure configured to transform symbols representing phonemes into sound representations, the method comprising identifying phonemes corresponding to a language utilized by a user, establishing a set of allowed sound frequencies, generating a correspondence mapping the identified phonemes to the set of allowed sound frequencies such that each constituent phoneme of the identified phonemes is assigned a subset of one or more frequencies from the set of allowed sound frequencies, and mapping each constituent phoneme of the identified phonemes to a set of one or more sounds. Establishing a set of allowed sound frequencies may comprise selecting a set of sound frequencies that are in a hearing range of the user. Each sound of the set of one more sounds may comprise an initial frequency parameter. Each sound of the set of one more sounds may comprise a begin time parameter. The begin time parameter may be representative of a time from an end of components of a previous sound representation. Each sound of the set of one more sounds may comprise an end time parameter. Each sound of the set of one more sounds may comprise a power parameter. Each sound of the set of one more sounds may comprise a power shift parameter. Each sound of the set of one more sounds may comprise a frequency shift parameter. Each sound of the set of one more sounds may comprise a pulse rate parameter. Each sound of the set of one more sounds may comprise a duty cycle parameter.

BRIEF DESCRIPTION OF THE DRAWINGS

FIG. 2 is a table of English phonemes shown in three nomenclatures.

FIG. 3A is a plot of sound intensity and sound frequency showing normal human hearing.

FIG. 3B is a plot of sound intensity and sound frequency showing hearing loss such as caused by chronic exposure to loud noise.

FIG. 3C is a plot of hearing level and sound frequency, as would appear in the form of a clinical audiogram, showing normal human hearing, and is analogous to the plot of FIG. 3A.

FIG. 3D is a plot of hearing level and sound frequency, as would appear in the form of a clinical audiogram, showing hearing loss such as caused by chronic exposure to loud noise, and is analogous to the plot of FIG. 3B.

FIG. 5A is a diagram showing a spectrogram, waveform and phonemes for an English word "chew"

FIG. 5B is a diagram similar to that of FIG. 5A but showing use of amplification in the spectrogram and waveform.

FIG. 5C is a diagram similar to that of FIG. 5A but showing use of speech processing in the spectrogram and waveform.

FIG. 5D is a diagram similar to that of FIG. 5A but showing use of phoneme substitution in the spectrogram and waveform.

FIG. 8 is a diagram of an example of a phoneme substitution data structure such as resulting from the assignment of sound sets to phonemes process shown in FIG. 7.

FIG. 13 is a diagram showing an embodiment of an implanted electrode array and an example structure of potential electrode assignments, such as stored in the database of nerve stimuli arrays to phonemes shown in FIG. 12.

FIG. 14A is a diagram of an embodiment of a skin interface, used with phoneme substitution, having mechanical or electrical stimulators fitted about a person's hand and wrist.

FIG. 14B is a diagram of an embodiment of a skin interface, used with phoneme substitution, having mechanical or electrical stimulators fitted about a person's wrist.

FIG. 15 is a table providing examples of mapping English phonemes to tactile symbols, such as for the skin interfaces shown in FIGS. 14A and 14B.

FIG. 16A is a diagram of various ways of representing the English word "chew".

FIG. 16B is a diagram showing embodiments of transmitters and receivers for implementing phoneme substitution communication, such as shown in FIGS. 6, 12 and 14A and 14B.

DETAILED DESCRIPTION OF CERTAIN EMBODIMENTS

Figure 1:
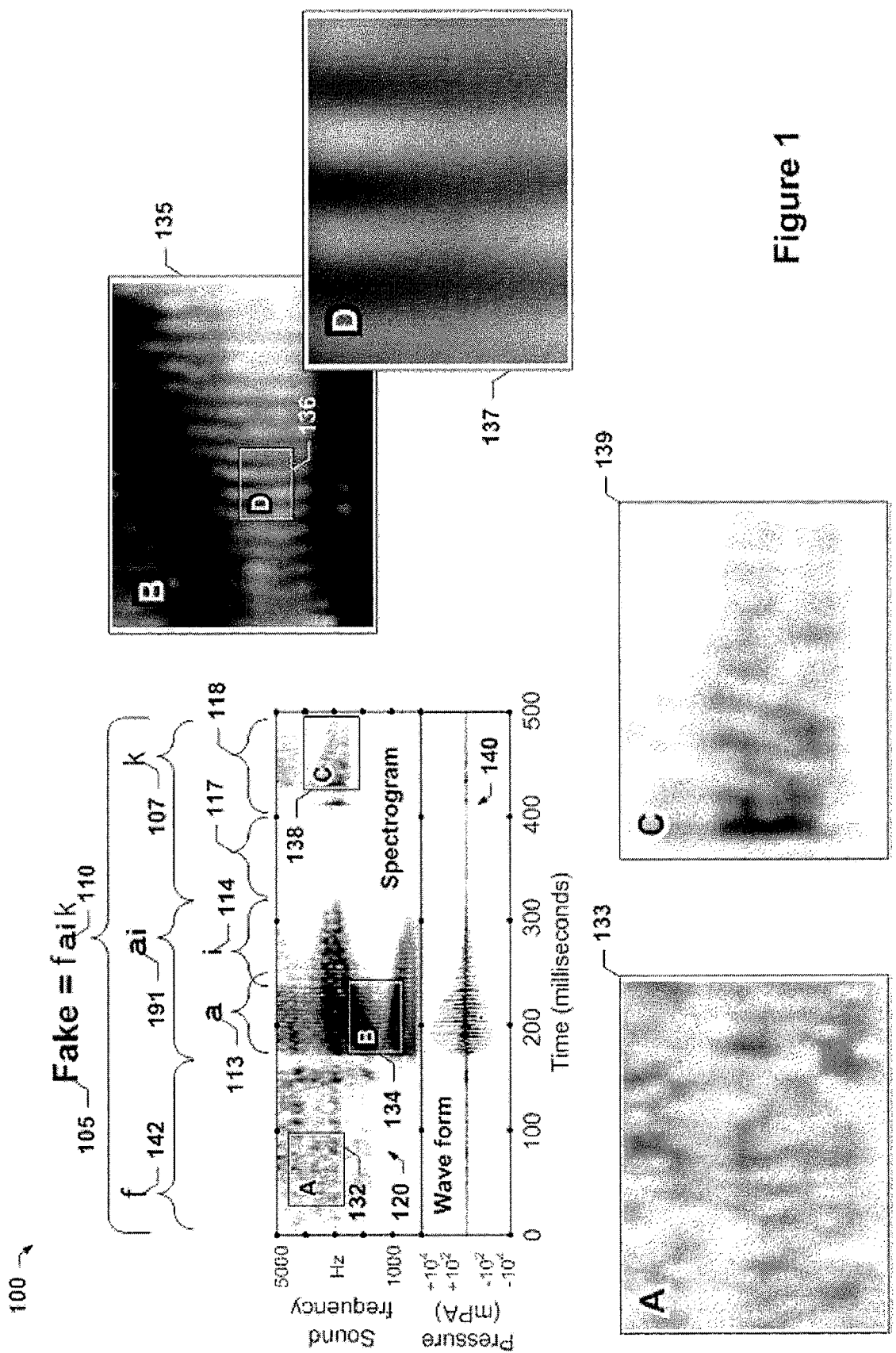
FIG. 1 is a diagram showing a spectrogram, waveform and phonemes for an English word.

The following detailed description of certain embodiments presents various descriptions of specific embodiments of the invention. However, the invention can be embodied in a multitude of different ways as defined and covered by the claims. In this description, reference is made to the drawings wherein like parts are designated with like numerals throughout.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

The system is comprised of various modules, tools, and applications as discussed in detail below. As can be appreciated by one of ordinary skill in the art, each of the modules may comprise various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system modules, tools, and applications may be written in any programming language such as, for example, C, C++, BASIC, Visual Basic, Pascal, Ada, Java, HTML, XML, or FORTRAN, and executed on an operating system, such as variants of Windows, Macintosh, UNIX, Linux, VxWorks, or other operating system. C, C++, BASIC, Visual Basic, Pascal, Ada, Java, HTML, XML and FORTRAN are industry standard programming languages for which many commercial compilers can be used to create executable code.

A computer or computing device may be any processor controlled device, which may permit access to the Internet, including terminal devices, such as personal computers, workstations, servers, clients, mini-computers, main-frame computers, laptop computers, a network of individual computers, mobile computers, palm-top computers, hand-held computers, set top boxes for a television, other types of web-enabled televisions, interactive kiosks, personal digital assistants, interactive or web-enabled wireless communications devices, mobile web browsers, or a combination thereof. The computers may further possess one or more input devices such as a keyboard, mouse, touch pad, joystick, pen-input-pad, and the like. The computers may also possess an output device, such as a visual display and an audio output. One or more of these computing devices may form a computing environment.

These computers may be uni-processor or multi-processor machines. Additionally, these computers may include an addressable storage medium or computer accessible medium, such as random access memory (RAM), an electronically erasable programmable read-only memory (EEPROM), programmable read-only memory (PROM), erasable programmable read-only memory (EPROM), hard disks, floppy disks, laser disk players, digital video devices, compact disks, video tapes, audio tapes, magnetic recording tracks, electronic networks, and other techniques to transmit or store electronic content such as, by way of example, programs and data. In one embodiment, the computers are equipped with a network communication device such as a network interface card, a modem, or other network connection device suitable for connecting to the communication network. Furthermore, the computers execute an appropriate operating system such as Linux, UNIX, any of the versions of Microsoft Windows, Apple MacOS, IBM OS/2 or other operating system. The appropriate operating system may include a communications protocol implementation that handles all incoming and outgoing message traffic passed over the Internet. In other embodiments, while the operating system may differ depending on the type of computer, the operating system will continue to provide the appropriate communications protocols to establish communication links with the Internet.

The computers may contain program logic, or other substrate configuration representing data and instructions, which cause the computer to operate in a specific and predefined manner, as described herein. A computer readable medium can store the data and instructions for the processes and methods described hereinbelow. In one embodiment, the program logic may be implemented as one or more object frameworks or modules. These modules may be configured to reside on the addressable storage medium and configured to execute on one or more processors. The modules include, but are not limited to, software or hardware components that perform certain tasks. Thus, a module may include, by way of example, components, such as, software components, object-oriented software components, class components and task components, processes, functions, attributes, procedures, subroutines, segments of program code, drivers, firmware, microcode, circuitry, data, databases, data structures, tables, arrays, and variables.

The various components of the system may communicate with each other and other components comprising the respective computers through mechanisms such as, by way of example, interprocess communication, remote procedure call, distributed object interfaces, and other various program interfaces. Furthermore, the functionality provided for in the components, modules, and databases may be combined into fewer components, modules, or databases or further separated into additional components, modules, or databases. Additionally, the components, modules, and databases may be implemented to execute on one or more computers. In another embodiment, some of the components, modules, and databases may be implemented to execute on one or more computers external to a website. In this instance, the website may include program logic, which enables the website to communicate with the externally implemented components, modules, and databases to perform the functions as disclosed herein.

The plots 100 of FIG. 1 illustrate one word in one language. Each language and dialect has its own set or sets of phonemes (different classification systems may define different sets of phonemes for the same language or dialect). The scope of this description encompasses all phonemes, both those currently defined and those not yet defined, for all languages.

As previously described, FIG. 2 is a table 200 of American English phonemes 225 shown in three nomenclatures: the International Phonics Association (IPA), s{mpA (a phonetic spelling of SAMPA, the abbreviation for Speech Assessment Methods Phonetic Alphabet), and the Merriam Webster Online Dictionary (m-w). Other nomenclatures, such as the Carnegie Mellon University pronouncing dictionary (cmudict), can be used in certain embodiments. Examples 226 of each phoneme as used in an American English word are provided, along with the manner 237 and place 247 of articulation 227.

Some embodiments relate to recoding phonemes to sets of sound frequencies that can be perceived by the user lacking the ability to hear the full range of human speech sounds.

FIG. 3A, plot 300a, shows a range of human hearing that is considered normal region 310a, on a plot of the sound frequency in Hertz (horizontal axis) versus the sound intensity in watts/m$^2$ (vertical axis). The threshold of perception is the bottom (low intensity) boundary 312a, 314a, which varies as a function of frequency. Human hearing is most sensitive to sound frequencies around 3000 Hz. At these frequencies, the threshold of perception 314a can be less than $10^{-12}$ watts/m$^2$ (0 dB) 341a for some individuals. The threshold of discomfort is the top (high intensity) boundary, 316a. The low frequency limit of human hearing is defined as the frequency that is both the threshold of perception and the threshold of discomfort 318a. The high frequency limit of human hearing 319a is defined in the same manner. For reference, the OSHA limit for safe long term exposure to noise in the work environment, 90 dB, is equivalent to $10^{-3}$ watts/m$^2$ 343a. Sound frequencies and intensities required for speech perception are generally between about 300 Hz and 9000 Hz and about $10^{-10}$ to $10^{-7}$ watts/m$^2$ (20 dB to 50 dB) region 320a. Lower frequencies area 323a are most important for the recognition of vowel sounds, while higher sound frequencies area 326a, are more important for the recognition of consonants (also see FIGS. 1 and 2).

Five to ten percent of people have a more limited hearing range shown in region 310 than that shown in FIG. 3A. Many different types of hearing impairments exist. For example, one or both ears may be affected in their sensitivities to different sound frequencies. Hearing impairments may be congenital or acquired later in life, and may result from, or be influenced by, genetic factors, disease processes, medical treatments, and/or physical trauma.

Exposure to loud noise causes irreversible damage to the human hearing apparatus. FIG. 3B, plot 300b, illustrates a reduced range of hearing region 310b as might result from chronic exposure to noise levels above 90 dB 343b. Although the threshold of perception for low frequency sounds 312b is only slightly affected, the ability to hear higher frequency sounds 314b is significantly impaired. A person with a hearing range as shown in FIG. 3B at region 310b, would be able to hear and recognize most low frequency vowel sounds at region 320b, but would find it difficult or impossible to hear and recognize many high frequency consonant sounds 330b. As a result, this person would be able to hear when people are speaking, but would be unable to understand what they are saying. For reference, the normal threshold of perception, 0 dB or $10^{-12}$ watts/m$^2$ is indicated by the arrow 341b and the OSHA limit for safe long term exposure to noise in the work environment, 90 dB or $10^{-3}$ watts/m$^2$, is indicated by the arrow 343b. Often, the threshold of discomfort 316b is relatively unaffected by a rise in the threshold of perception.

Often, hearing aids can improve speech recognition by amplifying speech sounds above the threshold of perception for hearing impaired persons. One embodiment is a device that recodes speech sounds to frequencies in a range of sensitive hearing rather than amplifying them at the frequencies where hearing is impaired. For example, an individual with a hearing range similar to that shown in FIG. 3B, region 300b, would not hear most speech sounds at frequencies above around 1500 Hz in region 330b, but could hear sounds recoded to sound frequencies around 400 Hz in area 350b.

Audiometry provides a practical and clinically useful measurement of hearing by having the subject wear earphones attached to the audiometer. Pure tones of controlled intensity are delivered to one ear at a time. The subject is asked to indicate when he or she hears a sound. The minimum intensity (volume) required to hear each tone is graphed versus frequency. The objective of audiometry is to plot an audiogram, a chart of the weakest intensity of sound that a subject can detect at various frequencies.

Although an audiogram presents similar information to the graphs in FIGS. 3A and 3B, it differs in several aspects. Although the human ear can detect frequencies from 20 to 20,000 Hz, hearing threshold sensitivity is usually measured only for the frequencies needed to hear the sounds of speech, 250 to 8,000 Hz. The sound intensity scale of an audiogram is inverted compared with the graphs in FIGS. 3A and 3B, and measured in decibels, dB, a log scale where zero has been arbitrarily defined as $10^{-12}$ watts/m$^2$. Also, the audiogram provides an individual assessment of each ear.

FIG. 3C, plot 300c, shows an audiogram for an individual with normal hearing, similar to that shown in FIG. 3A, plot 300a. A shaded area 320c represents the decibel levels and frequencies where speech sounds are generally perceived (the so-called "speech banana", similar to the shaded area of FIG. 3A, region 320a, but inverted). Hearing in the right ear is represented by circles connected by a line 362c and in the left ear by crosses connected by a line 364c. The symbols (circle for the right ear and cross for the left) indicate the person's hearing threshold at particular frequencies, e.g., the loudness (intensity) point where sound is just audible. Thresholds of perception from zero dB, shown by arrow 341c to 15 dB ($1.0 \times 10^{-12}$ to $3.2 \times 10^{-10}$ watts/m$^2$) are considered to be within the normal hearing range. The OSHA limit for safe long-term exposure to noise, 90 dB, or $10^{-3}$ watts/m$^2$, shown by arrow 343c, is also provided for reference. An area designated 323c indicates the range most important for hearing vowel sounds, and an area designated 326c indicates the range most important for hearing consonants.

FIG. 3D, plot 300d, shows an exemplary audiogram of an individual with bilaterally symmetrical hearing loss (similar hearing losses in both ears) similar to that shown in FIG. 3B, plot 300b. Hearing in the right ear is represented by circles connected by a line 362d and in the left ear by crosses connected by a line 364d. At the lower frequencies (250 to 500 Hz), little hearing loss has occurred, area 350d. However, at the mid-range of frequencies (500 to 1000 Hz) hearing loss is moderate, area 320d, and at the higher frequencies (>2000 Hz), hearing loss is severe, area 330d. A person with this degree of hearing loss would able to hear and recognize most low frequency vowel sounds, area 320d, but would find it difficult or impossible to hear and recognize many high frequency consonant sounds, area 330d. As a result, this person would be able to hear when people are speaking, but would be unable to understand what they are saying. Again, the normal threshold of perception, 0 dB or $10^{-12}$ watts/m$^2$, shown by arrow 341d, and the OSHA limit for safe long term exposure to noise in the work environment, 90 dB or $10^{-3}$ watts/m$^2$, shown by arrow 343d, are provided for reference.

Often, hearing aids can improve speech recognition by amplifying speech sounds above the threshold of perception for hearing impaired persons. An embodiment is a device that recodes speech sounds to frequencies in a range of sensitive hearing rather than amplifying them at the frequencies where hearing is impaired. For example, an individual with an audiogram similar to that shown in FIG. 3D, plot 300d, would not hear most speech sounds at frequencies above around 1500 Hz, area 330d, but could hear sounds recoded to sound frequencies around 400 Hz, area 350d.

There are many types of hearing aids, which vary in physical configuration, power, circuitry, and performance. They all aid sound and speech perception by amplifying sounds that would otherwise be imperceptible to the user; however, their effectiveness is often limited by distortion and the narrow range in which the amplified sound is audible, but not uncomfortable. Certain embodiments described herein overcome these limitations.

Figure 4A:
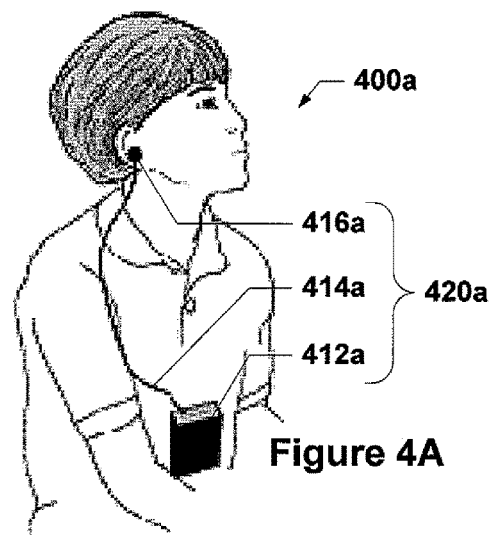
FIGS. 4A and 4B are diagrams showing conventional physical configurations of body-worn and in-the-ear hearing aids, respectively.
Figure 4B:
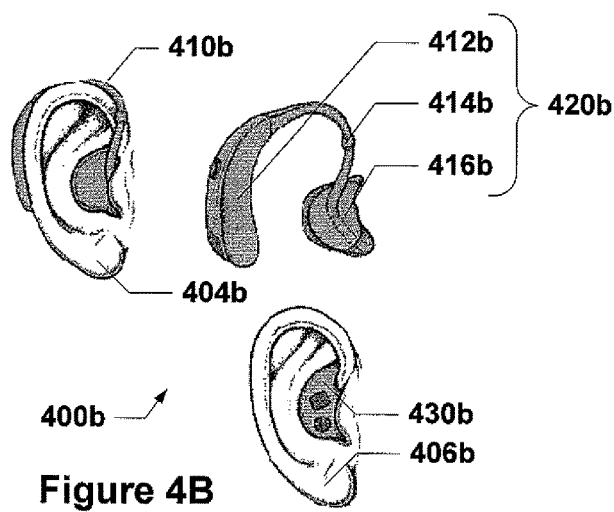

FIGS. 4A and 4B, diagrams 400a, 400b, illustrate some of the basic physical configurations found in hearing aid designs. A body worn aid 420a may comprise a case 412a containing a power supply and components of amplification; and an ear mold 416a containing an electronic speaker, connected to the case by a cord 414a. Behind-the-ear aids 410b, 420b may consist of a small case 412b containing a power supply, components of amplification and an electronic speaker, which fits behind an ear 404b; an ear mold 416b; and a connector 414b, which conducts sound to the ear 404b through the ear mold 416b. In-the-ear aids 430b comprise a power supply, components of amplification, and an electronic speaker, fit entirely within an outer ear 406b.

Figure 4C:
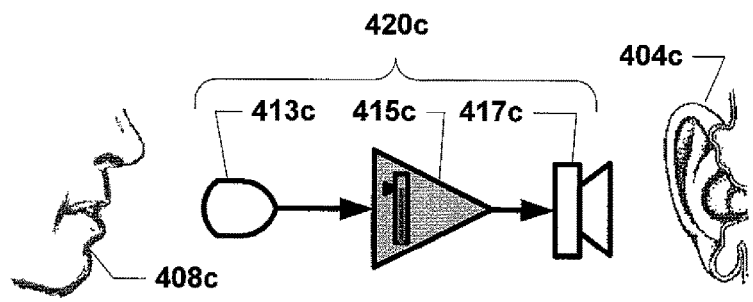
FIGS. 4C and 4D are diagrams showing functional components of low-complexity and medium-complexity hearing aids, respectively.
Figure 4D:
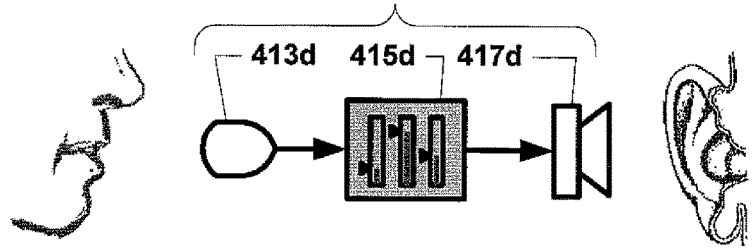

Operational principles of hearing aids may vary among devices, even if they share the same physical configuration. FIGS. 4C and 4D, diagrams 400c and 400d, illustrate some of the functional components found in hearing aid designs. The least complex device 420c comprises a microphone 413c, which converts sounds such as speech from another person 408c into an electronic signal. The electronic signal is then amplified by an amplifier 415c and converted back into sound by an electronic speaker 417c in proximity to the user's ear 404c.

More sophisticated devices 420d comprise a microphone 413d and a speaker 417d, which perform the same functions as their counterparts 413c, 417c respectively. However, sound and speech processing circuitry 415d can function differently from simple amplification circuitry 415c. Sound and speech processing circuitry 415d may be either digital or analog in nature. Unlike the simple amplifier 415c, sound and speech processing circuitry 415d can amplify different portions of the sound spectrum to different degrees. These devices might incorporate electronic filters that reduce distracting noise and might be programmed with different settings corresponding to the user's needs in different environments (e.g., noisy office or quiet room).

Figure 4E:
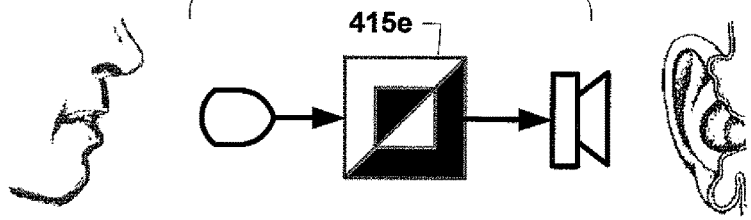
FIG. 4E is a diagram of a phoneme substitution based hearing aid.

An embodiment is shown in FIG. 4E, diagram 400e. A device 420e differs in its principle of operation from the hearing aids 420c and 420d in that its circuitry 415e can substitute the phonemes of speech sounds with unique sets of sounds (acoustic symbols). By substituting some or all of the phonemes in a given language with simple acoustic symbols, it is possible to utilize portions of the sound spectrum where a user may have relatively unimpaired hearing. The symbols themselves may represent phonemes, sets of phonemes, portions of phonemes, or types of phonemes. For an individual with an audiogram similar to that shown in FIG. 3D, the acoustic symbols could, for example, comprise sound frequencies between 200 Hz and 600 Hz, which would be audible to that person.

In FIG. 5, the English word, "chew", 505a, is used to compare and contrast certain embodiments described herein to conventional technologies. FIG. 5A, plots 500a provides a spectrogram 520a and waveform 540a for the word, "chew" 505a. When spoken, "chew" comprises two phonemes, tʃ, 524a, and u, 586a, which are visible as two distinctive regions 542a and 544a of the waveform 540a. However, as with the example for the English word, "fake", FIG. 1, plots 100, the waveform is too complex to expose much informative detail via visual inspection. The spectrogram 520a reveals a greater level of relevant detail. Here it is seen that the phoneme, tʃ 524a comprises a complex set of sound frequencies 521*a* broadly distributed largely above 3000 Hz. Most of the power for the phoneme, u, 586*a*, is contained in relatively tight frequency ranges around 500 Hz, 523*a*, and 2500 Hz, 522*a*. Additionally, u, 586*a*, is a voiced phoneme, exhibiting characteristic waxing and waning of power over many frequencies, observable as faint vertical stripes within the bands labeled 522*a* and 523*a*. The waxing and waning itself has a frequency of approximately 250 Hz (≈25 stripes per 100 milliseconds on the time axis).

An individual with an audiogram similar to that shown in FIG. 3D, plots 300*d*, might be able to hear the phoneme, u, 586*a*, reasonably well because its frequencies are in the lower range of speech. However, this individual would not hear tʃ 524*a* because this person's hearing is impaired at higher frequencies. A hearing aid using simple amplification can help to some extent by increasing the sound pressure (a.k.a. volume, a.k.a. power) at all frequencies as illustrated in FIG. 5B, plots 500*b*. As seen in the waveform, 540*b*, sound pressure has been increased for the phonemes, tʃ 542*b* and u, 544*b* relative to corresponding portions of the waveform 540*a*, 542*a* and 544*a*, FIG. 5A. The spectrogram reveals that low frequency sounds, 523*b*, have been amplified even though there is little or no need for amplification at these frequencies. This can result in distorted perception and discomfort for the user. Extraneous ambient noise is also amplified, as seen in area 528*b*, interfering with speech recognition and comfort.

FIG. 5C, plots 500*c*, illustrates a spectrogram 520*c* and waveform 540*c* obtained when the word, "chew" is spoken into a hearing aid with speech/sound processing capability. Increased amplitude is observed in the waveform area 542*c* but less so in the area 544*c* relative to corresponding portions of the waveform 540*a*, 542*a* and 544*a*, FIG. 5A. The spectrogram 520*c* reveals that most amplification occurs at the higher frequencies 521*c* and 522*c* but less so at the lower frequencies 523*c*. Therefore the low frequency components 523*c* of the phoneme u, 586*c* are not too loud. Noise problems are also reduced. However, the sound at 521*c* and 522*c* may be so loud that it is uncomfortable and could damage remaining hearing.

FIG. 5D, plots 500*d*, provides an example of a waveform, 540*d*, and spectrogram, 520*d*, as might result from recoding the word "chew" using the phoneme substitution method described herein. The waveform 540*d* and spectrogram 520*d* have been simplified relative to those in FIGS. 5A, 5B, and 5C, 540*a*, 520*a*, 540*b*, 520*b*, 540*c*, 520*c*, and all sound energy has been redirected to frequencies easily audible for an individual having an audiogram, plots 300*d*, similar to that shown in FIG. 3D. The portion of the waveform, 540*d*, corresponding to the phoneme, tʃ, 524*a*, is shown in waveform portion 542*d*, and that of the phoneme, u, 586*a*, is shown in waveform portion 544*d*. The spectrogram 520*d* shows a simple frequency distribution in a narrow range. All frequencies 531*d*, 532*d*, 533*d*, 536*d* and 537*d* are below 1000 Hz. Power at frequencies 536*d* and 537*d* representing the phoneme, u, 586*a*, is pulsed at a frequency of approximately 12 Hz.

Figure 6:
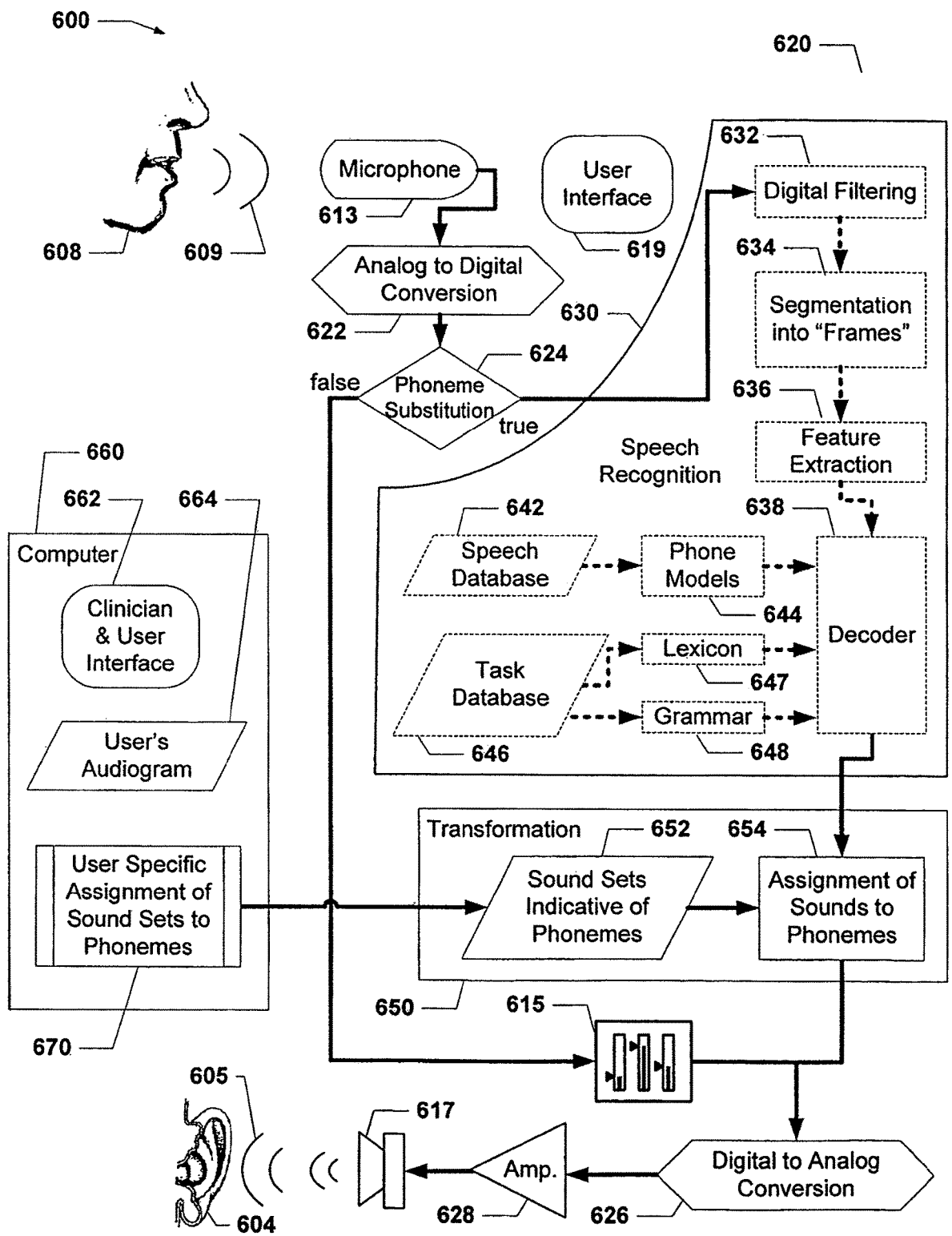
FIG. 6 is a diagram of an embodiment of the components associated with a hearing aid using phoneme substitution.

FIG. 6, diagram 600, provides an overview of how one embodiment transforms speech 609 (exemplified by the waveform illustrated in FIG. 5A, plots 500*a*) from a person speaking 608 in simple acoustic symbols 605 (exemplified in the waveform, 540*d*, illustrated in FIG. 5D, plots 500*d*) for a user 604 by use of a hearing aid 620. The components of the hearing aid 620 are described below.

The hearing aid 620 includes a microphone 613 to transform speech sound 609 into electronic analog signals which are then digitized by an analog to digital converter 622. The embodiment illustrated here provides a user interface 619 that allows the selection of one of two operating modes depending upon whether or not speech recognition is of primary interest to the user, 604, in any given setting. Other embodiments need not provide this option.

When speech recognition is of primary interest to the user 604, the value at decision state 624 will be true. A speech recognition process 630 transforms digitized speech sounds into digital symbols representing phonemes of the speech 609 produced by the person speaking 608. Characters representing phonemes are then exchanged for digital sound representations by a transformation process 650. The transformation process of transformer 650 can be performed by software, hardware or by combinations of software and hardware.

The transformation process 650 comprises a correspondence from a set of phonemes to a set of sound representations held in a database or other data structure 652 and a way 654 of generating sound representations corresponding to phonemes from the speech recognizer 630. The sounds representations held in the database 652 may be way files, mp3 files, aac files, aiff files, MIDI files, characters representing sounds, characters representing sound qualities, and the like.

The sound files are then converted to analog signals by a digital to analog process 626 amplified by an amplification process 628 and converted into audible sounds by a speaker 617.

When speech recognition is not of primary interest to the user 604, the value at decision state 624 will be false. The device will function as a digital hearing aid with conventional speech/sound processing functions 615, digital to analog signal conversion 626, amplification 628, and sound generation 617.

Although certain embodiments do not relate to the field of speech recognition technology, some embodiments utilize speech recognition. A number of strategies and techniques for building devices capable of recognizing and translating human speech into text are known to those skilled in such arts. For reference and background, a generic diagram of the inner workings of the speech recognizer, 630, as might be employed by some embodiments is provided in FIG. 6.

Within the speech recognizer 630, the digitized acoustic signal may be processed by a digital filter 632 in order to reduce the complexity of the data. Next, a segmentation process 634 parses the data into overlapping temporal intervals called frames. Feature extraction 636 involves computing a spectral representation (somewhat like a spectrogram) of the incoming speech data, followed by identification of acoustically relevant parameters such as energy, spectral features, and pitch information. A decoder 638 can be a search algorithm that may use phone models 644, lexicons 647, and grammatical rules 648, for computing a match between a spoken utterance 609 and a corresponding word string. While phonemes are the smallest phonetic units of speech, more fundamental units, phones, are the basic sounds of speech. Unlike phonemes, phones vary widely from individual to individual, depending on gender, age, accent, etc., and even over time for a single individual depending on sentence structure, word structure, mood, social context, etc. Therefore, phone models 644 may use a database 642, comprising tens of thousands of samples of speech from different individuals. A lexicon 647 contains the phonetic spellings for the words that are expected to be observed by the speech recognizer 630. The lexicon 647 serves as a reference for converting the phone sequences determined by the search algorithm into words. The grammar network or rules 648 defines the recognition task in terms of legitimate word combinations at the level of phrases and sentences. Some speech recognizers employ more sophisticated language models (not shown) that predict the most likely continuation of an utterance on the basis of statistical information about the frequency in which word sequences occur on average in the language. The lexicon 647 and grammar network 648 use a task database 646 comprising words and their various pronunciations, common phrases, grammar, and usage.

Referring again to the transformation process 650, because different users 604 may have different hearing requirements and abilities, the phonic symbol database 652 can be created and customized in consideration of each individual user 604. In some embodiments, a computer 660 can be used to aid in the creation of user specific phonic symbol databases, which are then downloaded to the database 652 of the hearing aid 620. The computer 660 comprises software allowing the input of data (e.g., audiogram) 664 from a user's hearing tests, a user interface 662, and a process or mapper 670 for creating a map (for database 652) to transform symbols representing phonemes into sets of sounds. In one embodiment, the mapper 670 can be performed by hardware circuits.

For some embodiments, each unique phoneme maps to a unique acoustic symbol. Each acoustic symbol comprises a unique set of sounds, each sound being audible the user, and each acoustic symbol, or sound set, having a distinctive perceived sound. The function of the Assignment Of Sound Sets to Phonemes process 670 in FIG. 6 is to build such a map. Process 670, further described in conjunction with FIG. 7, outlines one method for constructing the map. This and other methods can be performed manually or in an automated fashion using a computer or other computational device such as a table.

Acoustic symbols or sound sets may comprise one or more sounds. Sounds may differ in a number of qualities including but not limited to frequency, intensity, duration, overtones (harmonics and partials), attack, decay, sustain, release, tremolo, and vibrato. Although any or all of these differences can be employed, the example process 670 shown in FIG. 7 places a primary emphasis on variations in frequency. Therefore, the example process 670 provides acoustic symbols (sound sets) that are unique with respect to the sound frequencies they comprise. For simplicity, this example will employ only combinations of pure tones (no overtones). Sounds having harmonic content could be employed in a similar fashion.

Figure 7:
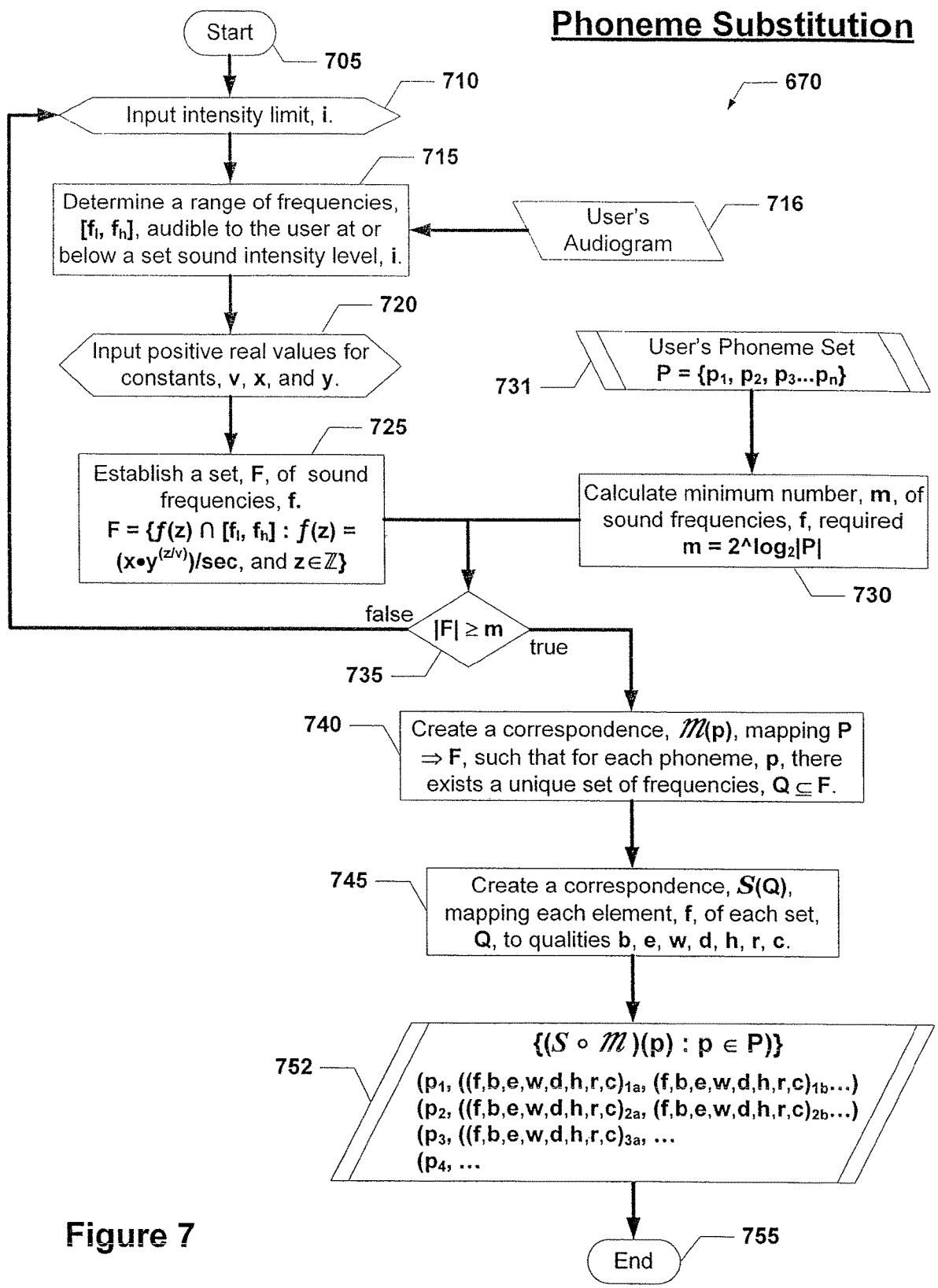
FIG. 7 is a flowchart of an embodiment of an assignment of sound sets to phonemes process shown in FIG. 6.

Referring to FIG. 7, following the start state 705 of process 670, state 710 calls for a value, i, the input intensity limit. The input intensity limit, i, is an intensity or power density level, above which the user should be able to perceive each and every sound present in the set of acoustic symbols. As the value for i is increased, the range of available sounds to construct acoustic symbols will increase.

Based upon data 716 from the user's hearing tests, state 715 determines a range of sound frequencies, It, $[f_l, f_h]$, such that each sound frequency in the range $[f_l, f_h]$, is perceptible to the user at power densities at or below i.

Human hearing is receptive to sound frequency changes in an approximately logarithmic fashion. Therefore, for some embodiments, it may be desirable to establish rules constraining the choices of sound frequencies used to construct phonic symbols. An example of such a rule could be that the set of allowed sound frequencies must not contain any two frequencies $f_1$ and $f_2$ such that $|(f_2-f_1)/(f_2+f_1)| \leq j$, where j is a constant between 0.02 and 0.1. To illustrate, if $[f_l, f_h] = [1000 \text{ Hz}, 2500 \text{ Hz}]$ and $j=0.038$, there would be 13 allowed frequencies. The closest any two frequencies could be at the low frequency end of the range would be 79 Hz, and the closest any two frequencies could be at the high frequency end of the range would be 183 Hz. More sophisticated rules can be used to factor in non-logarithmic and other components of the human hearing response to sound frequency.

Mathematical functions can be used to generate lists of allowed frequencies. For example, an equation, f(z), where $f(z)/f(z+1) = f(z+1)/f(z+2)$ for all integers, z, $(z \in \mathbb{Z})$ would generate a set of values evenly separated on a log scale. An example of such an equation is $f(z) = (x \cdot y\hat{}(z/v))/\text{sec}$, where v, x, and y are real numbers greater than one. For illustration purposes, if $x=2$, $y=10$, $v=2$, and $z \in \mathbb{Z}$, the equation, $f(z) = (x \cdot y\hat{}(z/v))/\text{sec}$, would generate the set { . . . 63 Hz, 200 Hz, 632 Hz, 2 kHz, . . . }. It may be noted that for $f(z) = (x \cdot y\hat{}(z/v))/\text{sec}$, values for y that are powers of 2 such as 2, 4, 8, etc. and values for v such as 3, 4, 6, 12, and 24 would yield frequencies separated by intervals approximating naturally occurring overtones and partials. Such sets of frequencies may give rise to sets of acoustic symbols more pleasing and perhaps discernable to the human ear.

Proceeding to state 720, process 670 calls for values of v, x, and y. Using the values of v, x, and y from state 720 and integer values for z, state 725 finds all sound frequencies that satisfy the equation and are greater than, $f_l$ but less than $f_h$. Stated symbolically, state 725 returns the set, $F = \{f(z \cap [f_l, f_h]: f(z) = (x \cdot y\hat{}(z/v))/\text{sec}, z \in \mathbb{Z}\}$. This equation is provided only as an example.

A database or data structure 731 comprises a list of phonemes that the user is likely to require. A person who uses only the English language might need approximately 39 phonemes as listed in FIG. 2, table 200. Someone who uses only the Hawaiian language would require approximately 13 phonemes while a person using two European and two Asian languages might require approximately 200 phonemes.

In this example, each symbol comprises a unique set of sound frequencies. Therefore, the composition of a given symbol either contains a particular sound frequency, or it doesn't. Therefore the maximum number of acoustic symbols that can be constructed from n frequencies is $2^n - 1$. For example, three different frequencies could yield up to seven unique symbols, while eleven frequencies could yield up to 2047 unique symbols. Conversely, the minimum number, m, of frequencies, f, needed to create a unique symbol for each phoneme, p, of a set of phonemes, P, is at least $2\hat{}\log_2 |P|$, where $|P|$ is the number of phonemes, p, in the set of phonemes, P.

State 730 determines the value of $|P|$ from the user's phoneme database 731, and returns a solution, m, for the above equation. Proceeding to a decision state 735 process 670 determines if the number of solutions, $|F|$, from state 725 is sufficient to create a unique acoustic symbol, or set of frequencies, for each element, p, in the user's phoneme set, P, from database 731. A value of false at decision state 735 returns the process 670 to the state 710. From there, the value for i may be increased thereby expanding the interval $[f_l, f_h]$, determined by state 715. Additionally, or alternatively, values for v, x, and y may be changed at state 720, to increase the number of solutions to the equation, $f(z) = (x \cdot y\hat{}(z/v))/\text{sec}$, that are within the range, $[f_l, f_h]$, determined by state 715. Decreasing the value for y, and/or increasing the value for v will tend to increase the number of solutions to $f(z) = (x \cdot y\hat{}(z/v))/\text{sec}$ within $[f_l, f_h]$. Adjusting the value for x in either direction may or may not alter the number of solutions to $f(z) = (x \cdot y\hat{}(z/v))/\text{sec}$ within $[f_l, f_h]$. When a change in the value of x does result in a change to the number of solutions to f(z)=(x·y^(z/v))/sec within [$f_l$, $f_h$], that number will increase or decrease by one solution (one allowed frequency).

A value of true at the decision state, 735, moves process 670 to state 740. State 740 is the first of two states 740 and 745 that assigns acoustic symbols, (sets of sounds) to phonemes.

In the first state 740, process 670 assigns to each phoneme a set of one or more allowed sound frequencies. More precisely, each phoneme, p, of the set of phonemes, P, is assigned a set, Q, of frequencies, f, each frequency, f, being an element of the set of allowed frequencies, F. Stated symbolically, state 740 returns a set, M={(p, Q): p∈P, Q ⊆F}.

In the second state 745, process 670 assigns additional qualities to be associated with each frequency element, f, of each frequency set, Q, of each element (p, Q) of the set, M. Seven variables are assigned in this example. In other embodiments, a different number of variables can be assigned.

b "begin" Sound at frequency, f, will start being produced b milliseconds after the end of the preceding acoustic symbol. If there is no preceding acoustic symbol, zero will be used in place of b. The variable, b, may have a value that is positive, negative, or zero.

e "end" Sound at frequency, f, will stop being produced e milliseconds after the end of the preceding acoustic symbol. If there is no preceding acoustic symbol, f, sound will stop being produced e milliseconds after it starts being produced.

w "power" Power at sound frequency, f, will be w decibels (dB) upon its initiation. 0 dB≡$10^{-12}$ watts/m$^2$ d "Δw" Power at sound frequency, f, will smoothly transition toward d·w decibels (dB) and will be d·w at the end of its duration. The variable, d, may have a value that is positive, negative, or zero.

h "Δf" Cycles per second at frequency, f, will smoothly transition from f Hertz (Hz) at its initiation to d·f Hz at the end of its duration. The variable, h, may have any value that is greater than zero; however values between 0.1 and 10 are most practical.

r "pulse rate" Power at sound frequency, f, will be reduced by at least 20 dB and restored to wdB r times each second.

c "duty cycle" The duty cycle variable, c, is the time within each pulse cycle that the power is equal to w divided by the time that the power is equal to or less than w−20 dB. A c value of 50% would produce a square wave.

At the conclusion of state 745, a data structure 752 is constructed mapping each phoneme to a set of sounds, each sound having eight parameters, f, b, e, w, d, h, r, c as described above. The completion of the data structure 752 allows progression to the end state 755.

In the above example, the various elements of the acoustic symbols were assembled about each phoneme. The order of these steps is not critical to the practice of certain embodiments described herein, and acoustic symbols may be predefined and later assigned to phonemes. The parameters, f, b, e, w, d, h, r, c are given only as examples.

To illustrate how the process 670 can operate, providing an intensity limit, i, value of 30 dB ($10^{-9}$ watts/m$^2$), and an audiogram 716 similar to that shown in FIG. 3D, plots 300*d*, would result in state 715, returning an interval of [80 Hz, 800 Hz]. If the values to state 720 are v=12, x=200, and y=2, state 740 would return the set of allowed frequencies, F, {84, 89, 94, 100, 106, 112, 119, 126, 133, 141, 150, 159, 168, 178, 189, 200, 212, 224, 238, 252, 267, 283, 300, 317, 336, 356, 378, 400, 424, 449, 476, 504, 534, 566, 599, 635, 673, 713, 755, 800}. If the user's phoneme set, P, comprises a minimal set of phonemes needed for American English, the number of elements, |P|, in the set, P, will be 39. State 730 would return the value, 2^$\log_2$39, which is 5.3. The number of elements, |F|, in the set, F, is 40. Because 40≥5.3, the Boolean value at decision state 735 is true, and process 670 would proceed to state 740. To simplify this example, the choice of frequencies will be further restricted to just nine of the 40 allowed frequencies, {300, 317, 336, 400, 424, 449, 504, 534, 566}.

In one embodiment, the symbols are unique combinations of one or more sound frequencies.

In another embodiment, the symbols are unique frequency intervals. A frequency interval is the absolute value log difference of two frequencies. Constructing acoustic symbols as frequency intervals has advantages as most people, including trained musicians, lack the ability to recognize individual sound frequencies but are able to recognize intervals.

In another embodiment, the combination of frequencies and their temporal modifications are unique for each symbol.

In another embodiment, the combination of frequency intervals and the temporal modifications for each frequency are unique for each symbol.

In another embodiment, the combination of frequencies and their timbre, which may comprise overtones (harmonics and partials), tremolo, and vibrato, is unique for each symbol.

In another embodiment, the combination of frequency intervals and the timbre of each frequency is unique for each symbol.

In another embodiment, phonemes are placed into groups of like phonemes (e.g., plosive, fricative, diphthong, monophthong, etc.). Such a placement of phonemes into groups of like phonemes is known to linguists and others skilled in such arts. All phonemes are then assigned a sound frequency (the root), all phonemes being given the same root. Each member of each group of like phonemes is given a second frequency unique to that group. Once all phonemes have been assigned a second sound frequency, the most frequently used phoneme of each group is not assigned additional sound frequencies. Therefore, the most frequently used phonemes are represented by single frequency intervals. One or more additional sound frequencies are then assigned to the remaining phonemes to create a unique combination of frequencies for each phoneme.

In another embodiment, phonemes are placed into groups of like phonemes (e.g., plosive, fricative, diphthong, monophthong, etc.). Such a placement of phonemes into groups of like phonemes is known to linguists and others skilled in such arts. All phonemes are then assigned a sound frequency (the root), all phonemes being given the same root. Each member of each group of like phonemes is given a second frequency unique to that group. Once all phonemes have been assigned a second sound frequency, the most frequently used phoneme of each group is not assigned additional sound frequencies. Therefore, the most frequently used phonemes are represented by single frequency intervals. One or more additional sound frequencies are then assigned to the remaining phonemes to create a unique combination of frequencies for each phoneme. Next, every frequency of every phoneme in one group of like phonemes is shifted up or down by multiplying every frequency of every phoneme in one group of like phonemes by a constant.

Additional groups of like phonemes may or may not be adjusted in a similar fashion using the same constant or a different constant.

In another embodiment, the acoustic symbol's frequencies, intervals, temporal modifiers, and/or timbre, may be selected to resemble features of the phoneme from which it was derived. For example, the fricative, s, might be assigned a higher frequency or frequencies, than the vowel, ɜ; plosives might all have the modifier, g=2; voiced phonemes might have the modifier, b=2; and unvoiced phonemes might have the modifier, b=1. Frequencies, intervals, temporal modifiers, timbre, and other qualities may be applied methodically, arbitrarily, or randomly.

FIG. 8 illustrates an exemplary example data structure 752 as might be returned by state 745, FIG. 7. The data structure 752 contains examples of the use of sound qualities listed above. Not all of the sound qualities in the example are required to practice certain embodiments described herein, and other qualities not listed here may be employed.

In this example, the data structure comprises ordered sets, each ordered set matching a phoneme, p, to one or more sounds. Each sound is defined by an ordered set comprising values for the variables f, b, e, w, d, h, r, c. To facilitate cross-referencing, the last two digits of each callout or reference label in FIG. 8 are the same as the last two digits of corresponding phonemes in FIGS. 1, 2, 5, 9, 11, 15, and 16. The time scale as well as nature of the symbols does however vary from figure to figure.

Figure 9:
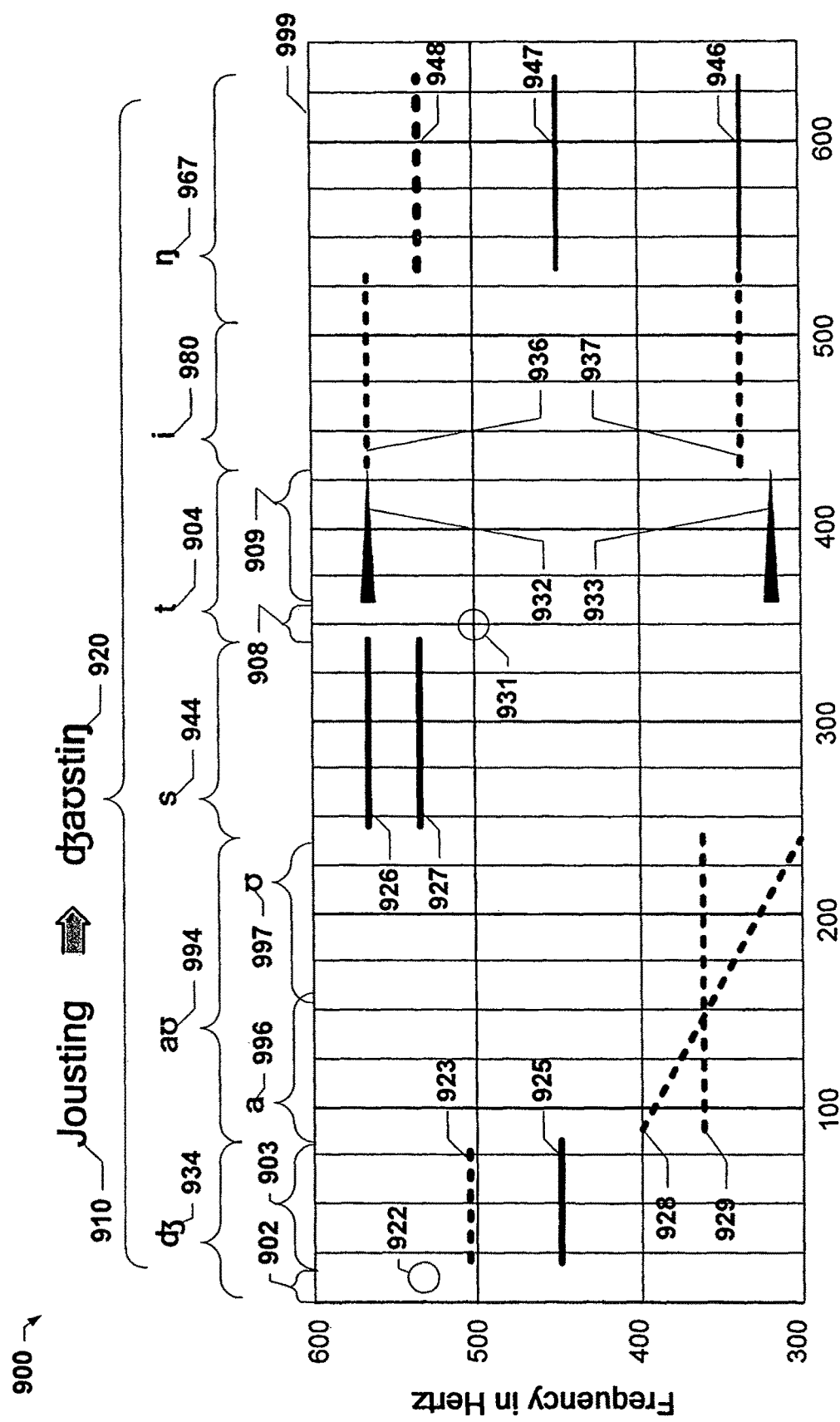
FIG. 9 is a plot of a spectrogram for the English word "jousting" as a result of phoneme substitution such as performed using the data structures shown in FIG. 8.

Referring to FIGS. 8 and 9, the word jousting will used in the next example. The IPA representation of the word, "jousting", is "ʤaʊstiŋ", and comprises seven phonetic symbols, ʤ, a, ʊ, s, t, i, and ŋ. However, the monophthong, "a", 996 (FIG. 9), is not used as a sole vowel sound in American English words or syllables, but exists only as part of the diphthongs, ai, and aʊ. Therefore, in English "ʤaʊstiŋ", 920, actually comprises just six phonemes, ʤ, aʊ, s, t, i, and ŋ.

When state 654, FIG. 6, searches the data structure 652 or 752, FIG. 8, it finds the ordered sets;
 (ʤ,(449,20,90,50,0,1,100,100),(504,20,90,50,0,1,90,50))
 (aʊ,(317,0,150,50,0,1,84,67),(400,0,150,50,0,0.75,84,67))
 (s,(534,0,100,50,0,1,100,100),(566,0,100,50,0,1,100,100))
 (t,(317,20,90,50,−30,1,100,100),(566,20,90,50,−30,1,100,100))
 (i,(336,0,100,50,0,1,100,67),(566,0,100,50,0,1,100,67))
 (ŋ,(336,0,100,50,0,1,100,100),(449,0,100,50,0,1,100,100),(534,0,100,60,0,1,126,80))
 (FIG. 8 callouts 834, 894, 844, 804, 880, 867, respectively).
and returns the sets of sound definitions;
 [(449,20,90,50,0,1,100,100),(504,20,90,50,0,1,90,50)]
 [(317,0,150,50,0,1,84,67),(400,0,150,50,0,0.75,84,67)]
 [(534,0,100,50,0,1,100,100),(566,0,100,50,0,1,100,100)]
 [(317,20,90,50,−30,1,100,100),(566,20,90,50,−30,1,100,100)]
 [(336,0,100,50,0,1,100,67),(566,0,100,50,0,1,100,67)]
 [(336,0,100,50,0,1,100,100),(449,0,100,50,0,1,100,100),(534,0,100,60,0,1,126,80)]
which are converted into 630 milliseconds of analog signal by the digital to analog state 626, amplified by the analog amplifier 628, and converted into sound 605 by the speaker 617.

FIG. 9 provides a schematic representation 900 of a spectrogram 999 of the sound 605 emitted by the speaker 617 (FIG. 6), after transformation 650 of the word "jousting" via the assignment state 654, drawing upon the data structure 652 or 752 (FIG. 8). To show detail, the vertical axis spans 300 Hz to 600 Hz rather than 0 Hz to 5000 Hz as in FIGS. 1 and 5. Also, power is depicted through line thickness rather than color intensity, thicker lines representing greater power.

As stated above, the IPA representation of the English word, "jousting", 910, is "ʤaʊstiŋ", 920, and comprises seven phonetic symbols, ʤ, 934, a, 996, ʊ, 997, s, 944, t, 904, i, 980, and ŋ, 967. In American English the phonemes are, ʤ, 934, aʊ, 994, s, 944, t, 904, i, 980, and ŋ, 967.

The first phoneme, ʤ, 934, is represented by an acoustic symbol defined by an ordered set of two ordered sets of eight elements, each defining a sound components of the acoustic symbol, [(449,20,90,50,0,1,100,100),(504,20,90,50,0,1,90,50)]. This definition calls for two sounds 925 and 923. The first sound 925 defined by the ordered set (449,20,90,50,0,1,100,100), has a constant frequency, h=0, of 449 Hz, f=449, a constant power, d=0, of 50 dB, w=50, starting after a 20 ms, b=20, delay 902 and 922 from the end of the previous acoustic symbol, and ending 90 ms, e=90, after the end of the previous acoustic symbol, and not pulsed, c=100. The value for r, pulse rate, is 100, but may be any positive value in this instance because a 100% duty cycle, c=100, obviates pulse rate. Read in the same manner, the second ordered set, (504,20,90,50,0,1,90,50), defines a sound 923 having a constant frequency of 504 Hz, a constant power of 50 dB, starting 20 ms after the end of the previous acoustic symbol, and ending 90 ms after the end of the previous acoustic symbol, and pulsed, at a frequency of 90 Hz r=90, and a 50% duty cycle, c=50.

The next ordered set of ordered sets, [(317,0,150,50,0,1,84,67), (400,0,150,50,0,0.75,84,67)] defines an acoustic symbol comprising two sounds 929 and 928 representing a ʊ, 994. The first sound 929, defined by the ordered set, (317,0,150,50,0,1,84,67), has a constant frequency of 317 Hz, a constant power of 50 dB, starting immediately, b=0, after the end of the previous acoustic symbol 923 and 925, and ending 150 ms after the end of the previous acoustic symbol 923 and 925, and pulsed, at a frequency of 84 Hz r=84, and a 67% duty cycle, c=67. The second ordered set, (400,0,150,50,0,0.75,84,67), defines a sound 928 having an initial frequency of 400 Hz, f=400, a final frequency of 300 Hz, h=0.75, and 400•0.75=300, a constant power of 50 dB, starting 0 ms after the end of the previous acoustic symbol, ending 150 ms after the end of the previous acoustic symbol, and pulsed, at a frequency of 84 Hz r=84, with a 67% duty cycle, c=67.

The next phoneme, s, 944, is represented by two un-pulsed sounds, one at 534 Hz, 927, and the other at 566 Hz, 926, each having a constant power of 50 dB, lasting 100 ms.

The phoneme, t, 904, is represented by two un-pulsed sounds, 933 and 932, starting 20 ms, 908 and 931, after the acoustic symbol representing the phoneme, s. Initial power for each is 50 dB, w=50, and final power for each to 20 dB, d=−30, 50−30=20.

The phoneme, i, 980, is represented by two pulsed sounds, 937 and 936.

The final acoustic symbol, defined by the ordered set of ordered sets, [(336,0,100,50,0,1,100,100),(449,0,100,50,0,1,100,100),(534,0,100,60,0,1,126,80)], comprises three sounds. One sound 948 is pulsed, and two sounds 947 and 946 are not. Also, the sound at 534 Hz, 948, is 10 dB louder that than the other two sounds 947 and 946.

Figure 10A:
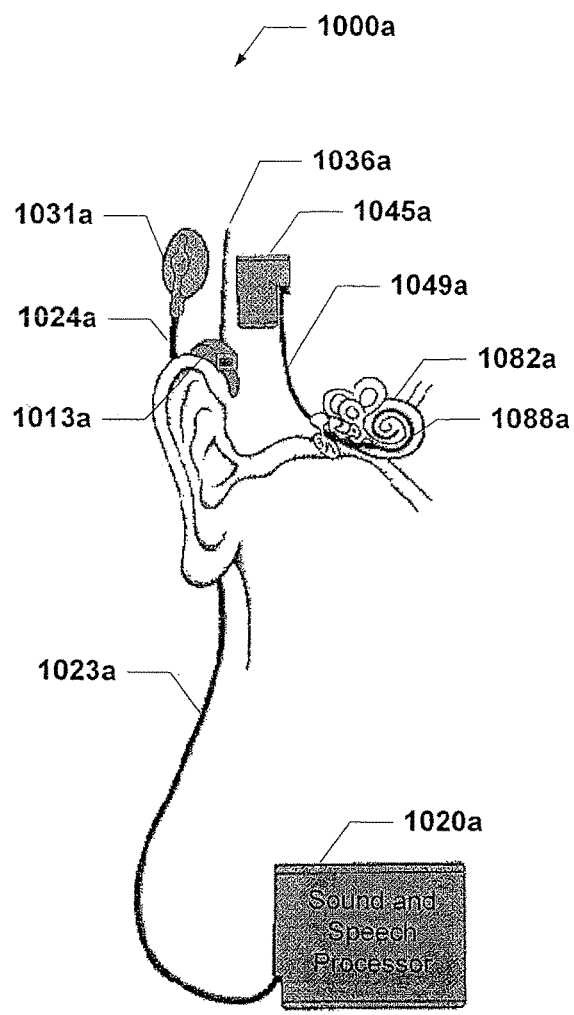
FIG. 10A is a diagram of physical components of an example of a cochlear implant hearing device.
Figure 10B:
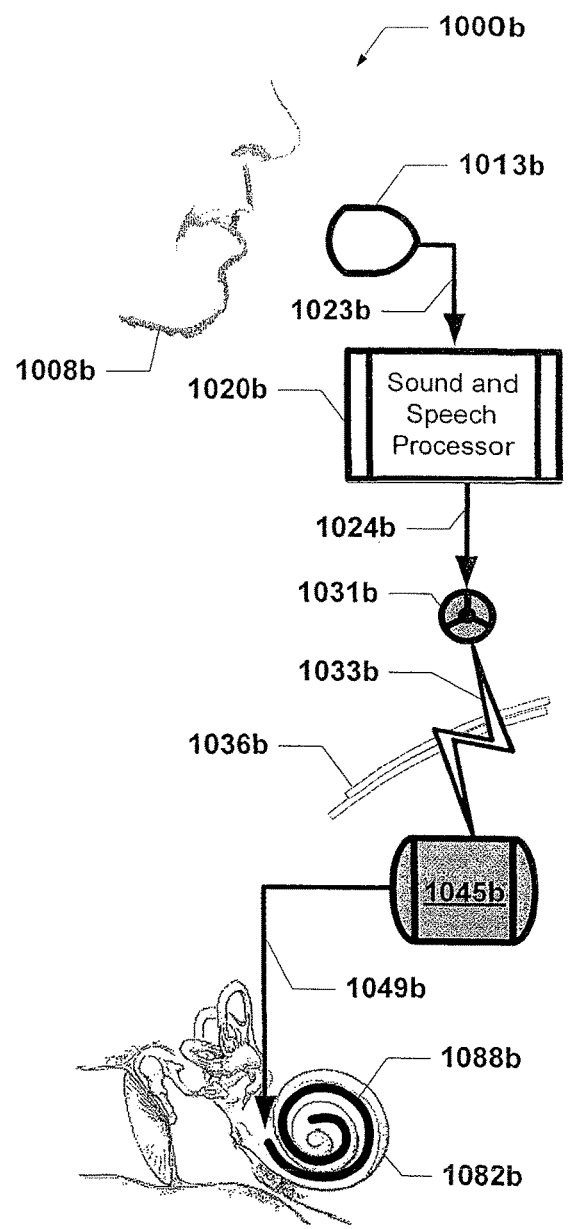
FIG. 10B is a diagram of a functional configuration of the example cochlear implant hearing device shown in FIG. 10A.

FIG. 10a illustrates a configuration 1000a of a cochlear implant hearing aid device and FIG. 10b shows a schematic representation 1000b of this device. A microphone 1013a, 1013*b* transforms speech and other sounds into electrical signals that are conveyed to a sound and speech processor 1020*a*, 1020*b* via an electrical cable 1023*a*, 1023*b*. The sound and speech processor unit 1020*a*, 1020*b* also houses a power supply for external components 1013*a*, 1013*b*, 1031*a*, 1031*b* and implanted components 1045*a*, 1045*b* of the cochlear implant hearing aid device. The sound and speech processor 1020*a*, 1020*b* can contain bandpass filters to divide the acoustic waveforms into channels and convert the sounds into electrical signals. These signals go back through a cable 1024*a*, 1024*b* to a transmitter 1031*a*, 1031*b* attached to the head by a magnet, not shown, within a surgically implanted receiver 1045*a*, 1045*b*.

The transmitter 1031*a*, 1031*b* sends the signals and power from the sound and speech processing unit 1020*a*, 1020*b* via a combined signal and power transmission 1033*b* (and similarly for 1000*a*) across the skin 1036*a*, 1036*b* to the implanted receiver 1045*a*, 1045*b*. Using the power from the combined signal and power transmission 1033*b*, the receiver 1045*a*, 1045*b* decodes the signal component of the transmission 1033*b* and sends corresponding electrical waveforms through a cable 1049*a*, 1049*b* to an electrode array 1088*a*, 1088*b* surgically placed in the user's cochlea 1082*a*, 1082*b*. The electrical waveforms stimulate local nerve tissue creating the perception of sound. Individual electrodes, not shown, are positioned at different locations along the array 1088*a*, 1088*b*, allowing the device to deliver different stimuli representing sounds having different pitches, and importantly, having the sensation of different pitch to the user.

The effectiveness of a cochlear prosthesis depends to a large extent on the stimulation algorithm used to generate the waveforms sent to the individual electrodes of the electrode array 1088*a*, 1088*b*. Stimulation algorithms are generally based on two approaches. The first places an emphasis on temporal aspects of speech and involves transforming the speech signal into different signals that are transmitted directly to the concerned regions of the cochlea. The second places an emphasis on spectral speech qualities and involves extracting features, such as formants, and formatting them according to the cochlea's tonotopy (the spatial arrangement of where sound is perceived).

Certain embodiments apply to novel stimulation algorithms for a cochlear prosthesis. These algorithms substitute some or all temporal and spectral features of natural speech for a small number (such as in a range of 10 to 500) of symbols, comprising the waveforms to be sent to the electrode array, 1088*a*, 1088*b*.

Figure 11A:
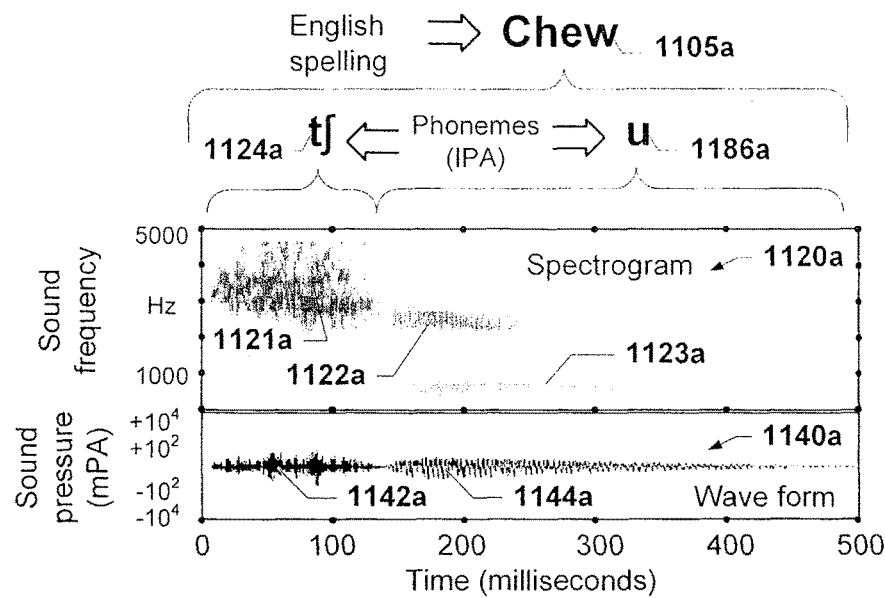
FIG. 11A is a diagram showing a spectrogram, waveform and phonemes for an English word "chew"

In FIG. 11, the English word, "chew" 1105*a* is used to compare and contrast certain embodiments described herein to conventional stimulation algorithms. In FIG. 11A, plots 1100*a* provide a spectrogram 1120*a* and waveform 1140*a* for the word "chew" 1105*a*.

For a person with normal hearing, the cochlea provides the brain with detailed information about the speech signal shown by waveform 1140*a*. Within the cochlea the original sound waveform 1140*a* is lost in the process of being transformed into nerve impulses. These nerve impulses actually contain little information describing the actual waveform 1140*a*, but instead, convey detailed information about power as a function of time and frequency. Therefore, a spectrogram such as spectrogram 1120*a*, but not a waveform, is a convenient representation of the information conveyed through the auditory nerve to the auditory cortex of the brain.

A cochlear prosthesis (see FIG. 10) can restore a level of hearing to a person whose cochlea is not functional, but still has a functional auditory cortex and auditory nerve innervating the cochlea. The cochlear prosthesis electrically stimulates nervous tissue in the cochlea, resulting in nerve impulses traveling along the auditory nerve to the auditory cortex of the brain. Although hearing can often be successfully restored to deafened individuals, speech recognition often remains challenging.

Limitations in speech perception arise from limitations of the implanted portion of the prosthesis. Normally, the cochlea divides the speech signal into several thousand overlapping frequency bands that the auditory cortex uses to extract speech information. Prior cochlear implants are able to provide a speech signal divided into just a dozen or so frequency bands. As a result, much of the fine spectral detail is lost as many frequency bands are blended into a few frequency bands. The auditory cortex is thereby deprived of much of the speech information it normally uses to identify features of spoken language.

Figure 11B:
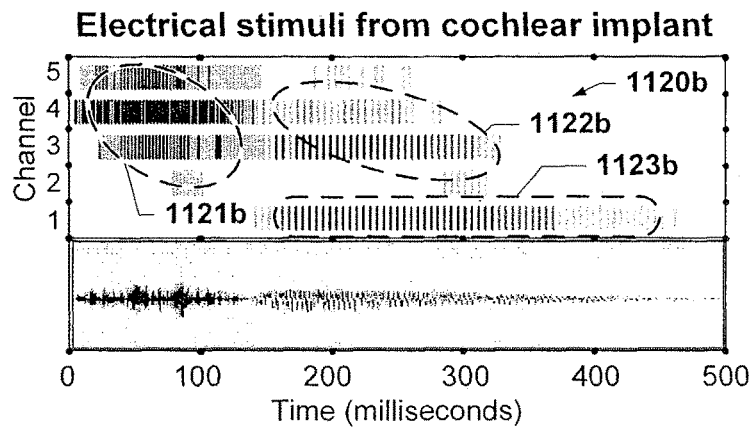
FIG. 11B is a diagram similar to that of FIG. 11A but showing use of conventional sound processing in the spectrogram.

In FIG. 11B, plots 1100*b* schematically illustrate the spectral resolution and detail of a speech signal shown by a spectrogram 1120*b* generated by a conventional cochlear prosthesis. Gross temporal and spectral features are similar to that of natural speech shown by the spectrogram 1120*a*. However, spectrally important portions 1121*b*, 1122*b*, 1123*b* of the phonemes tʃ, 1124*a* and u, 1186*a* lack the fine detail seen in the natural speech example shown at portions 1121*a*, 1122*a*, 1123*a*.

To ameliorate this problem, stimulation algorithms are used to help convey speech information through the limited number of frequency bands or channels. Stimulation algorithms are generally based on two approaches. The first places an emphasis on temporal aspects of speech and involves transforming the speech signal into different signals that are transmitted directly to the concerned regions of the cochlea. The second places an emphasis on spectral speech qualities and involves extracting features, such as formants, and formatting them according to the cochlea's tonotopy (the spatial arrangement of where sound is perceived). Current stimulation algorithms do help, but are unable to provide most users with speech recognition comparable to that of those with normal hearing.

Certain embodiments apply to novel stimulation algorithms for cochlear prostheses. These algorithms substitute some or all temporal and spectral features of natural speech for a small number (approximately 20 to 100) of symbols, comprising the waveforms to be sent to the electrode array 1088*a*, 1088*b* as shown in FIG. 10. The symbols themselves may represent phonemes, sets of phonemes, or types of phonemes.

Figure 11C:
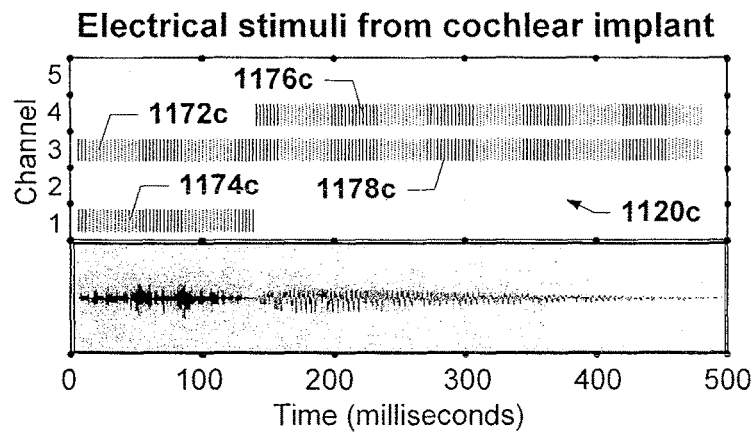
FIG. 11C is a diagram similar to that of FIG. 11A but showing use of phoneme substitution in the spectrogram.

In FIG. 11C, plots 1100C schematically illustrate a speech signal shown by spectrogram 1120*c* as might result from recoding for the word "chew" 1105*a* using a phoneme substitution method of certain embodiments described herein. The symbols may, but do not need to, preserve some spectral and temporal features of the natural speech signal shown by the spectrogram 1120*a*. The conventional stimulation algorithm shown by plots 1100*b* approximates spectral features 1121*a* of the phoneme, tʃ, 1124*a*, and spectral features 1122*a*, 1123*a* of the phoneme, u, 1186*a* in corresponding areas 1121*b*, 1122*b*, 1123*b*. In contrast, a speech signal generated using a stimulation algorithm employing phoneme substitution does not approximate spectral features 1121*a*, of the phoneme, tʃ, 1124*a*, and spectral features 1122*a*, 1123*a* of the phoneme, u, 1186*a* in its corresponding areas 1172*c*, 1174*c*, 1176*c*, 1178*c*.

An advantage of certain embodiments described herein is that, in principle, the speech signal will not vary from speaker to speaker and location to location. Another advantage is that the speech signal is no longer more complicated than the language based information it contains. Both features result in speech signals that are easier to learn and recognize than those generated using current state-of-the-art stimulation algorithms.

Figure 12:
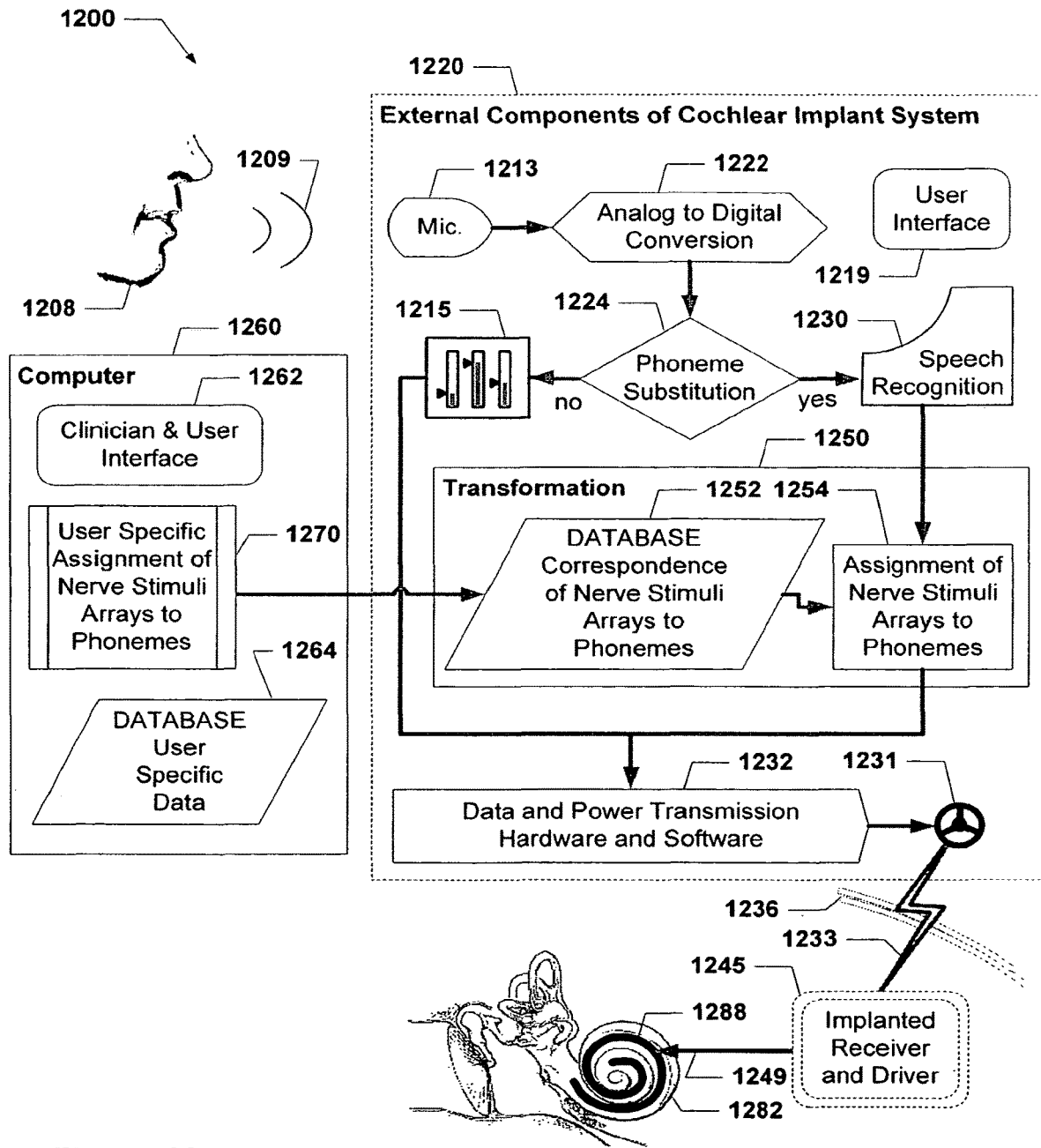
FIG. 12 is a diagram of an embodiment of the components associated with a hearing implant using phoneme substitution.

FIG. 12 provides an overview diagram 1200 of how one embodiment transforms speech 1209 (exemplified by the waveform illustrated in FIG. 11A by spectrogram 1100a) from a person speaking 1208 into simple symbols (exemplified in the speech signal illustrated in FIG. 11C by spectrogram 1120c) that are delivered to an electrode array of a user's cochlear implant 1288. The transformation is performed by external components of a cochlear implant system such as sound and speech processing unit 1220.

The sound and speech processing unit or processor 1220 includes a microphone 1213 to transform speech sounds 1209 into electronic analog signals that are then digitized by an analog to digital converter 1222. The embodiment illustrated here provides a user interface 1219 that allows the selection of one of at least of two operating modes depending upon whether or not speech recognition is of primary interest to the user, in any given setting. Other embodiments need not provide this option.

When speech recognition is of primary interest to the user, the value at decision state 1224 will be true. A speech recognition process 1230 transforms digitized speech sounds into digital characters representing phonemes of the speech 1209 produced by the person speaking 1208. Characters representing phonemes are then exchanged for digital representations of stimulation patterns by a transformation process 1250. The transformation process or transformer 1250 can be performed by software, by hardware, or by combinations of software and hardware.

The transformation process 1250 comprises a correspondence from a set of phonemes to stimulation patterns held in a database or other data structure 1252 and a process 1254 for generating a sequence of representations of stimulation patterns corresponding to a sequence of phonemes from the speech recognizer 1230.

The digital representations are sent to a data and power transmitter 1231 and 1232 attached to the user's head by a magnet, not shown, within a surgically implanted receiver 1245.

The transmitter 1231 and 1232 sends the signals and power from the sound and speech processing unit 1220 via a combined signal and power transmission 1233 across the skin 1236 to the implanted receiver 1245. Using the power from the combined signal and power transmission 1233, the receiver 1245 decodes the signal component of the transmission 1233 and sends corresponding electrical waveforms through a cable 1249 to the electrode array 1288 surgically placed in the user's cochlea 1282.

When speech recognition is not of primary interest to the user, the value at decision state 1224 will be false, and the device will function using other stimulation algorithms 1215.

Although certain embodiments do not relate to the field of speech recognition technology, some embodiments utilize speech recognition. A number of strategies and techniques for building devices capable of recognizing and translating human speech into text are known to those skilled in such arts. For reference, FIG. 6 provides a generic diagram 600 of the inner workings of a speech recognizer 630 as might be employed by some embodiments.

Because different users may have different requirements and abilities, the database 1252 of representations of stimulation patterns can be created and customized in consideration of each individual user. In some embodiments, a computer 1260 can be used to aid in the creation of user databases, which are then downloaded to the database memory 1252 of the sound and speech processing unit 1220.

The computer 1260 comprises software allowing the input of data 1264 from a user's hearing tests, a user interface 1262 and a process or mapper 1270 for creating a map to be stored in the database 1252 to transform symbols representing phonemes into digital representations of stimulation patterns.

The process 1270 for creating the map to transform symbols representing phonemes into digital representations of stimulation patterns is similar to the process 670 shown in FIG. 6, and defined in FIG. 7. The process 1270 can be considered a modified version of process 670 in which the interval $[f_l, f_h]$, is replaced with a set, G, of functional electrodes, $\{g_n, g_{n+1}, g_{n+2}, \ldots\}$ of the electrode array 1288. The set, F, then becomes the subset of G, its elements representing electrodes rather than frequencies.

FIG. 13 is a diagram 1300 showing an example structure of potential electrode assignments 1352, such as stored in database 1252, for one embodiment in which the user wishes to comprehend American English speech. The upper portion of the figure shows the middle and inner ear 1360 including the cochlea 1365. Within the cochlea 1365 is an implanted electrode array 1320 of a cochlear prosthesis.

For illustration purposes, it is assumed that the electrode array 1320 comprises 16 electrodes, nine of which, 1303, 1304, 1305, 1306, 1307, 1308, 1309, 1310, 1311, are functional and able to produce unique sound sensations for the user. In this example, 39 American English phonemes are mapped using the exemplary data structure 1352 (stored in 1252, FIG. 12) to stimulation patterns (symbols) comprising electrical waveforms being sent to different combinations of one, two, or three electrodes.

For simplicity, other qualities used in the preceding examples of hearing aids are not contained in the structure 1352. However, analogs of each are envisioned for embodiments relating to hearing prosthesis including cochlear implants. These analogs and others include, but are not limited to, pauses between some phonemes, duration, intensity, low frequency pulsations or higher frequency signals, stimulus rates, and shifts in the values of such parameters as a function of time, or context.

The symbols themselves may represent phonemes, sets of phonemes, portions of phonemes, or types of phonemes.

In one embodiment, the symbols are unique combinations of stimuli at one or more electrodes. In another embodiment, the symbols are unique physical spacings of stimuli. In another embodiment, the combination of electrodes used and other qualities including, but are not limited to, pauses between some phonemes, duration, intensity, low frequency pulsations or higher frequency signals, stimulus rates, and shifts in the values of such parameters as a function of time, are unique for each symbol.

In another embodiment, phonemes are placed into groups of like phonemes (e.g., plosive, fricative, diphthong, monophthong, etc.). Such a placement of phonemes into groups of like phonemes is known to linguists and others skilled in such arts. All phonemes are then assigned a common electrode or channel (the root), all phonemes being given the same root. Each member of each group of like phonemes is assigned a second channel unique to that group. Once all phonemes have been assigned a second channel, the most frequently used phoneme of each group is not assigned additional channels. Therefore, the most frequently used phonemes are represented by unique combinations of two channels. One or more additional channels are then assigned to the remaining phonemes to create a unique combination of channels for each phoneme.

In another embodiment, phonemes are placed into groups of like phonemes (e.g., plosive, fricative, diphthong, monophthong, etc.). Such a placement of phonemes into groups of like phonemes is known to linguists and others skilled in such arts. All phonemes are then assigned a common electrode or channel (the root), all phonemes being given the same root. Each member of each group of like phonemes is assigned a second channel unique to that group. Once all phonemes have been assigned a second channel, the most frequently used phoneme of each group is not assigned additional channels. Therefore, the most frequently used phonemes are represented by unique combinations of two channels. One or more additional channels are then assigned to the remaining phonemes to create a unique combination of channels for each phoneme. Next, every channel assignment for every phoneme in one group of like phonemes is shifted up or down along the electrode array. Additional groups of like phonemes may or may not be adjusted in a similar fashion.

The concept of phoneme substitution can be applied to sensory tissues other than the cochlea. These can include but are not limited to pressure, pain, stretch, temperature, photo and olfactory receptor tissue as well as innervating nerves tissue and corresponding central nervous system tissue.

For example, phonic symbols may be delivered to sensory tissue of the skin, by a number of means, including electrical and mechanical means. FIGS. 14A and 14B provide schematic examples 1400a and 1400b of skin interfaces 1410a and 1410b of some embodiments.

FIG. 14A, example 1400a, shows an interface 1410a fitted about the hand and wrist of a person's left arm 1450a for example. The interface 1410a comprises six stimulators 1401a, 1402a, 1403a, 1404a, 1405a, 1406a positioned against the person's skin 1440a. In this example, the stimulators have been placed as to assure that no two are close to being positioned over the same receptive field, the smallest area of skin capable of allowing the recognition of two different but similar stimuli. In one embodiment the stimulators 1405a and 1406b are located under the wrist of the user.

FIG. 14B, example 1400b, shows an interface 1410b fitted about the wrist of a person's left arm 1450b for example. The interface 1410b comprises six stimulators 1401b, 1402b, 1403b, 1404b, 1405b, 1406b positioned against the person's skin 1440b, some close enough to each other to be on the outer threshold of occupying same receptive field. In one embodiment the stimulators 1405b and 1406b are located under the wrist of the user.

Creating a correspondence mapping phonemes to sets of tactile stimuli, symbols, is not fundamentally different from mapping phonemes to acoustic symbols of hearing aid embodiments or electrical stimulation patterns of cochlear prosthesis embodiments. FIG. 15, table 1500, provides three examples for mapping English phonemes to tactile symbols suitable for use with the tactile interfaces 1410a and 1410b presented in FIG. 14. To better illustrate concepts not yet described, each of the three maps uses the same channel assignments, and each stimulator generates a motion of vibration perpendicular to the skin.

These maps were created using methods previously described but not illustrated. The first step for all three examples is to place phonemes into a group of like phonemes (e.g., plosive, fricative, diphthong, monophthong, etc.). These groups are known to linguists and others skilled in such arts.

For example 1, each group is then assigned a channel, for example plosive=1, nasal=2, fricative=3, approximant=4, monophthong=5, diphthong=6. Affricates, being both plosive and fricative like, are assigned both channels 3 and 4. No further channel assignments are made to the most frequently used member of each set, t, n, s, ɹ, ʌ, and eɪ. These assignments can be made by linguists and others skilled in such arts. Additional channels are assigned to other phonemes creating a unique combination of channel assignments corresponding to each. An advantage in this approach is that training can begin with the use of only six symbols, each comprising a vibration at a single location on the skin.

In example 2, the channel assignments for each phoneme are the same as in example 1. However for each tactile symbol representing a phoneme, the channel common to all members of its group of related phonemes is vibrated at a different frequency than the other channels comprising that symbol. These stimulators are indicated by boxes in the column for example 2. The advantage in this approach is that phonemes that sound most alike will feel most alike, and thereby enhance the learning process, and reduce errors.

In example 3, even numbered stimulators vibrate at one frequency, and odd numbered stimulators vibrate at a different frequency. Odd numbered channels are highlighted with a box for better visualization of the figure. The advantage in this approach is that adjacent stimulators have a different feel, and therefore may be placed in closer proximity to one another, while maintaining the ability to create a sensation unique to each channel. A logical extension of this approach is to use only three stimulators, each having three states, off, on frequency 1, and on frequency 2.

For simplicity, other qualities used in the preceding examples of hearing aids and implants are not contained in the three data structures shown in FIG. 15. However, analogs of each quality are envisioned for embodiments relating to skin and interfaces. These analogs and others include, but are not limited to, pauses between some phonemes, duration, intensity, low frequency pulsations or higher frequency signals, stimulus rates, and shifts in the values of such parameters as a function of time, or context.

In one embodiment, the symbols are unique combinations of stimuli at one or more electrodes. In another embodiment, the symbols are unique physical spacings of stimuli. In another embodiment, the combination of electrodes used, and other qualities including, but are not limited to, pauses between some phonemes, duration, intensity, low frequency pulsations or higher frequency signals, stimulus rates, and shifts in the values of such parameters as a function of time, are unique for each symbol.

In another embodiment, phonemes are placed into groups of like phonemes (e.g., plosive, fricative, diphthong, monophthong, etc.). Such a placement of phonemes into groups of like phonemes is known to linguists and others skilled in such arts. All phonemes are then assigned a common electrode or channel (the root), all phonemes being given the same root. Each member of each group of like phonemes is assigned a second channel unique to that group. Once all phonemes have been assigned a second channel, the most frequently used phoneme of each group is not assigned additional channels. Therefore, the most frequently used phonemes are represented by unique combinations of two channels. One or more additional channels are then assigned to the remaining phonemes to create a unique combination of channels for each phoneme.

In another embodiment, phonemes are placed into groups of like phonemes (e.g., plosive, fricative, diphthong, monophthong, etc.). Such a placement of phonemes into groups of like phonemes is known to linguists and others skilled in such arts. All phonemes are then assigned a common electrode or channel (the root), all phonemes being given the same root. Each member of each group of like phonemes is assigned a second channel unique to that group. Once all phonemes have been assigned a second channel, the most frequently used phoneme of each group is not assigned additional channels. Therefore, the most frequently used phonemes are represented by unique combinations of two channels. One or more additional channels are then assigned to the remaining phonemes to create a unique combination of channels for each phoneme. Next, every channel assignment for every phoneme in one group of like phonemes is shifted up or down along the electrode array. Additional groups of like phonemes may or may not be adjusted in a similar fashion.

FIG. 16A, via plots 1600a, shows the word "chew" 1605a; its component phonemes, tʃ, 1624a; and u, 1686a; a waveform 1635a obtained when "chew" is spoken; "chew" written in machine shorthand 1645a; "chew" as it appears in acoustic symbols generated by the phoneme substitution method described herein 1655a; "chew" as it might be encoded by phoneme substitution and then transmitted to electrodes in a cochlear implant 1665a; "chew" as it might be transmitted to electrodes on a skin interface 1675a; and "chew" as it might be perceived in the form of its component phonemes by the user. FIG. 16B, diagram 1600b, illustrates embodiments as transmitters 1605b, 1635b, 1645b and receivers 1655b, 1665b, 1675b. A computer 1605b is shown transmitting the typed word "chew" to a hearing aid 1655b; cochlear implant 1665b; or skin interface 1675b. The waveform produced by a person speaking 1635b is shown being transmitted to 1655b, 1665b, and 1675b. The shorthand machine 1645b is shown transmitting a signal to 1655b, 1665b, and 1675b.

There are embodiments that do not require mapping of phonemes to unique symbols or sets of stimuli. Simply mapping each phoneme to a symbol or set of stimuli unique to it and similar phonemes may be helpful to hearing impaired individuals. For example, many people with hearing impairments have some proficiency in lip reading, or speech reading. Others may be relatively proficient in vowel recognition, but have a difficult time with the recognition of consonants. The phonetic structure of the six words, two, do, sue, zoo, and new, is tu, du, su, zu, and nu, respectively. These five words differ appreciably only in their first phoneme, a consonant. However, all five words appear the same on a speaker's lips. Simply knowing which type of phoneme the initial consonant is would be enough information to disambiguate these words for an individual with relatively good low frequency hearing or proficiency in speech reading. In fact, simply knowing if the initial consonant is a plosive, fricative, and/or voiced is sufficient to discriminate between each word in the list.

CONCLUSION

While specific blocks, sections, devices, functions and modules may have been set forth above, a skilled technologist will realize that there are many ways to partition the system, and that there are many parts, components, modules or functions that may be substituted for those listed above. While the above detailed description has shown, described, and pointed out the fundamental novel features of the invention as applied to various embodiments, it will be understood that various omissions and substitutions and changes in the form and details of the system illustrated may be made by those skilled in the art, without departing from the intent of the invention.

What is claimed is:

1. A system for processing a sequence of spoken words into stimulation of a part of a user's body using a sequence of sets of nerve stimuli, each set of nerve stimuli being a symbolic representation of a phoneme of a particular user's language, the system comprising:
    a converter configured to receive a sequence of spoken words and to digitize electrical signals representative of the sequence of spoken words;
    a speech recognizer configured to receive the digitized electrical signals and generate a sequence of phonemes representative of the sequence of spoken words, wherein a number of possible phonemes in a phoneme set for a particular user is based on a spoken language used by the particular user;
    a mapper configured to receive a particular user's audiogram and to assign a symbolic representation to each phoneme, utilizing the particular user's audiogram to select one common pool of a minimum number of stimuli from which each symbolic representation is constructed, each symbolic representation comprising between one and the minimum number of stimuli selected from the one common pool so as to generate a map, wherein each of the selected between one and the minimum number of stimuli has a set of corresponding acoustic parameters, and wherein the particular user's audiogram is used to determine a range of sound frequencies such that each sound frequency in the range is perceptible to the particular user at a selected input power density limit, wherein first rules implemented by the mapper constrain a set of sound frequencies within the determined range of sound frequencies;
    a transformer configured to receive the sequence of phonemes representative of the sequence of spoken words and the map and to generate a sequence of stimulus definitions corresponding to the sequence of phonemes; and
    a receiver configured to obtain and convert the sequence of stimulus definitions into electrical waveforms used to stimulate a part of the particular user's body according to the sequence of stimulus definitions such that the sequence of spoken words can be discerned by the particular user.

2. The system of claim 1,
    wherein the receiver comprises a digital to analog converter.

3. The system of claim 2, wherein the receiver additionally comprises an amplifier and a transducer.

4. The system of claim 2, additionally comprising an electrode array configured to receive the electrical waveforms, wherein the electrode array comprises a plurality of mechanical stimulators.

5. The system of claim 2, additionally comprising an electrode array configured to receive the electrical waveforms, wherein the electrode array comprises a plurality of electrodes.

6. The system of claim 1, wherein the sequence of stimulus definitions comprise digital representations of nerve stimulation patterns.

7. The system of claim 1, wherein the mapper configured to assign the symbolic representation to each phoneme utilizes a list of phonemes based on the language of the particular user.

8. The system of claim 1, wherein, for the English language, the map comprises thirty-nine combinations of nerve stimuli mapped to thirty-nine phonemes, wherein each of the thirty-nine combinations of nerve stimuli comprise between one to six individual stimulus, wherein each of the thirty-nine combinations of nerve stimuli are derived from the common pool, wherein the common pool includes six individual stimuli.

9. The system of claim 1, wherein the nerve stimuli are associated with a hearing prosthesis.

10. The system of claim 9, wherein the hearing prosthesis comprises a cochlear implant.

11. The system of claim 10, wherein each symbolic representation includes electrode assignments.

12. The system of claim 1, wherein the stimulus definitions comprise sets of one or more stimuli.

13. The system of claim 12, wherein each stimulus of the sets of one or more stimuli comprises a begin time parameter, wherein a value of the begin time parameter is not based on a refractory period of human ear nerve fibers.

14. The system of claim 13, wherein the begin time parameter is representative of a time from an end of components of a previous stimulus definition.

15. The system of claim 12, wherein each stimulus of the sets of one or more stimuli comprises an end time parameter, wherein a value of the end time parameter is not based on a refractory period of human ear nerve fibers.

16. The system of claim 15, wherein the end time parameter has a value in a range between 90 milliseconds and 150 milliseconds.

17. The system of claim 15, wherein the end time parameter has a value in a range between 45 milliseconds and 75 milliseconds.

18. The system of claim 1, wherein the acoustic parameters include a begin time, an end time, a power at a frequency of a particular stimulus, a change in power between the begin time and the end time at the frequency of the particular stimulus, a change in cycles per second between the begin time and the end time of the frequency of the particular stimulus, a pulse rate of a stimulus of a particular power at the frequency of the particular stimulus, and a duty cycle.

19. The system of claim 1, wherein the first rules implemented by the mapper generate a set of sound frequency values evenly separated on a log scale.

20. The system of claim 1, wherein the minimum number of stimuli is expressed by $\log_2$ (the number of phonemes in the phoneme set for the particular user).

21. The system of claim 1, wherein the acoustic parameters include frequency, duration, intensity and stimulus rates.

22. The system of claim 1, wherein the selecting between one and the minimum number of stimuli from the common pool is constrained by second rules implemented by a mathematical formulation.

23. The system of claim 22, wherein the second rules implemented by the mathematical formulation generate a second set of one or more sound frequencies, within the determined range of sound frequencies, for each phoneme.

24. The system of claim 1, wherein each symbolic representation corresponding to a particular phoneme has between one and the minimum number of stimuli assigned, wherein the values of each acoustic parameter of the set of acoustic parameters can vary for each phoneme.

25. The system of claim 1, wherein the receiver comprises a digital to analog converter and an amplifier.

26. A system for processing a sequence of spoken words into stimulation of a part of a user's body using a sequence of sets of nerve stimuli, each set of nerve stimuli being a symbolic representation of a phoneme of a particular user's language, the system comprising:

a converter configured to receive a sequence of spoken words and to digitize electrical signals representative of a sequence of spoken words;

a speech recognizer configured to receive the digitized electrical signals and generate a sequence of phonemes representative of the sequence of spoken words, wherein a number of possible phonemes in a phoneme set for a particular user is based on a spoken language used by the particular user;

a mapper configured to receive a particular user's audiogram and to assign a symbolic representation to each phoneme, utilizing the particular user's audiogram to select one common pool of six stimuli from which each symbolic representation is constructed, each symbolic representation comprising between one and six stimuli selected from the one common pool so as to generate a map, wherein each of the selected one to six stimuli has a set of corresponding acoustic parameters, and wherein the particular user's audiogram is used to determine a range of sound frequencies such that each sound frequency in the range is perceptible to the particular user at a selected input power density limit, wherein first rules implemented by the mapper constrain a set of sound frequencies within the determined range of sound frequencies;

a transformer configured to receive the sequence of phonemes representative of the sequence of spoken words and the map and to generate a sequence of stimulus definitions corresponding to the sequence of phonemes; and a receiver configured to receive and convert the sequence of stimulus definitions into electrical waveforms used to stimulate a part of the particular user's body according to the sequence of stimulus definitions such that the sequence of spoken words can be discerned by the particular user.

27. The system of claim 26, wherein the acoustic parameters include a begin time, an end time, a power at a frequency of a particular stimulus, a change in power between the begin time and the end time at the frequency of the particular stimulus, a change in cycles per second between the begin time and the end time of the frequency of the particular stimulus, a pulse rate of a stimulus of a particular power at the frequency of the particular stimulus, and a duty cycle.

* * * * *